(12) United States Patent
Konya et al.

(10) Patent No.: US 9,017,620 B2
(45) Date of Patent: Apr. 28, 2015

(54) COMBINATION DRIVE FOR A SAMPLING SYSTEM FOR COLLECTING A LIQUID SAMPLE

(75) Inventors: Ahmet Konya, Waldsee (DE); Herbert Harttig, Neustadt (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1077 days.

(21) Appl. No.: 12/727,720

(22) Filed: Mar. 19, 2010

(65) Prior Publication Data

US 2010/0216246 A1    Aug. 26, 2010

Related U.S. Application Data

(63) Continuation of application No. PCT/EP2008/062547, filed on Sep. 19, 2008.

(30) Foreign Application Priority Data

Sep. 19, 2007  (EP) ..................................... 07116748

(51) Int. Cl.
| | |
|---|---|
| *A61B 5/151* | (2006.01) |
| *G01N 35/10* | (2006.01) |
| *G01N 33/50* | (2006.01) |
| *A61B 5/15* | (2006.01) |
| *A61B 5/145* | (2006.01) |
| *A61B 5/157* | (2006.01) |

(52) U.S. Cl.
CPC ........... *A61B 5/1411* (2013.01); *A61B 5/14532* (2013.01); *A61B 5/14546* (2013.01); *A61B 5/157* (2013.01); *A61B 2562/0295* (2013.01)

(58) Field of Classification Search
None
See application file for complete search history.

(56) References Cited

U.S. PATENT DOCUMENTS

| | | |
|---|---|---|
| 4,442,836 A | 4/1984 | Meinecke et al. |
| 5,318,584 A | 6/1994 | Lange et al. |
| 5,554,166 A | 9/1996 | Lange et al. |

(Continued)

FOREIGN PATENT DOCUMENTS

| | | |
|---|---|---|
| CA | 2311496 | 6/1999 |
| DE | 103 32 488 A1 | 2/2005 |

(Continued)

OTHER PUBLICATIONS

International Preliminary Report on Patentability, PCT/EP2008/062547.

*Primary Examiner* — Jill Warden
*Assistant Examiner* — Benjamin Whatley
(74) *Attorney, Agent, or Firm* — Bose McKinney & Evans LLP

(57) ABSTRACT

A sampling system for collecting a liquid sample, having at least one analytic auxiliary means is proposed. The sampling system has a coupling element for coupling onto the analytic auxiliary means and at least one drive unit for driving a movement of the coupling element from a rest position into a deflected position. The drive unit comprises an energy transducer which is designed to generate a rotational movement with different rotational directions. The drive unit furthermore has a coupling device with at least one rotational-direction sensitive element, wherein the coupling device is designed to couple the energy transducer to a first system function in a first rotational direction, and to couple said transducer to a second system function which differs from the first system function in a second rotational direction which differs from the first rotational direction.

26 Claims, 14 Drawing Sheets

(56) References Cited

U.S. PATENT DOCUMENTS

| | | |
|---|---|---|
| 5,846,837 A | 12/1998 | Thym et al. |
| 6,036,919 A | 3/2000 | Thym et al. |
| 6,988,996 B2* | 1/2006 | Roe et al. .................. 600/584 |
| 2002/0169470 A1 | 11/2002 | Kuhr et al. |
| 2002/0188224 A1* | 12/2002 | Roe et al. .................. 600/584 |
| 2003/0083685 A1* | 5/2003 | Freeman et al. ............ 606/181 |
| 2005/0090850 A1* | 4/2005 | Thoes et al. ................ 606/182 |
| 2006/0002816 A1 | 1/2006 | Zimmer et al. |
| 2006/0155317 A1* | 7/2006 | List ............................ 606/181 |
| 2006/0173380 A1* | 8/2006 | Hoenes et al. .............. 600/583 |
| 2006/0178600 A1* | 8/2006 | Kennedy et al. ............ 600/584 |
| 2006/0195128 A1* | 8/2006 | Alden et al. ................ 606/181 |
| 2006/0216817 A1 | 9/2006 | Hoenes et al. |
| 2007/0219572 A1 | 9/2007 | Deck et al. |
| 2008/0167578 A1* | 7/2008 | Bryer et al. ................ 600/583 |
| 2009/0149725 A1* | 6/2009 | Gofman et al. ............. 600/309 |
| 2011/0130782 A1* | 6/2011 | Kan et al. .................. 606/182 |

FOREIGN PATENT DOCUMENTS

| | | |
|---|---|---|
| DE | 103 43 896 A1 | 4/2005 |
| EP | 0 565 970 A1 | 10/1993 |
| EP | 1 424 040 A1 | 6/2004 |
| EP | 1 669 028 A1 | 6/2006 |
| WO | WO 97/02487 A1 | 1/1997 |
| WO | WO 98/48695 A1 | 11/1998 |
| WO | WO 2004/056269 A1 | 7/2004 |
| WO | WO 2004/060174 A2 | 7/2004 |
| WO | WO 2005/107596 A2 | 11/2005 |
| WO | WO 2006/013045 A1 | 2/2006 |

* cited by examiner

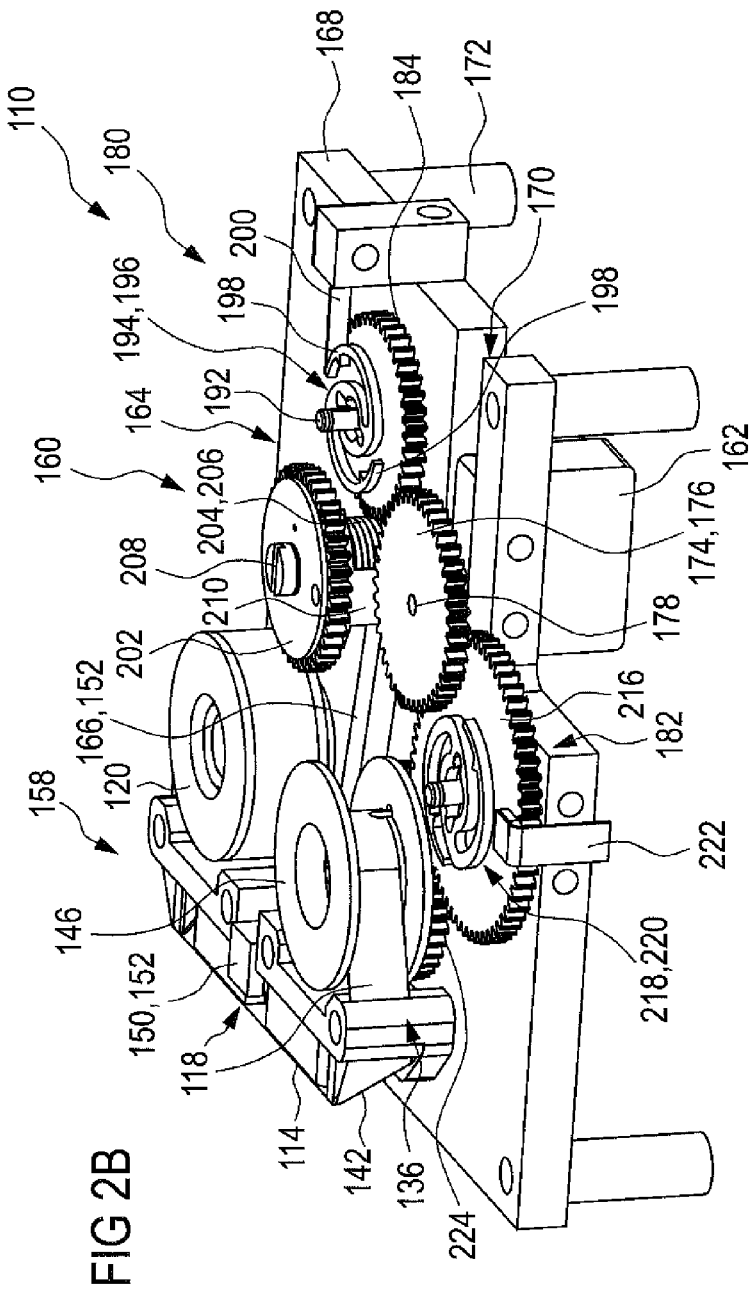

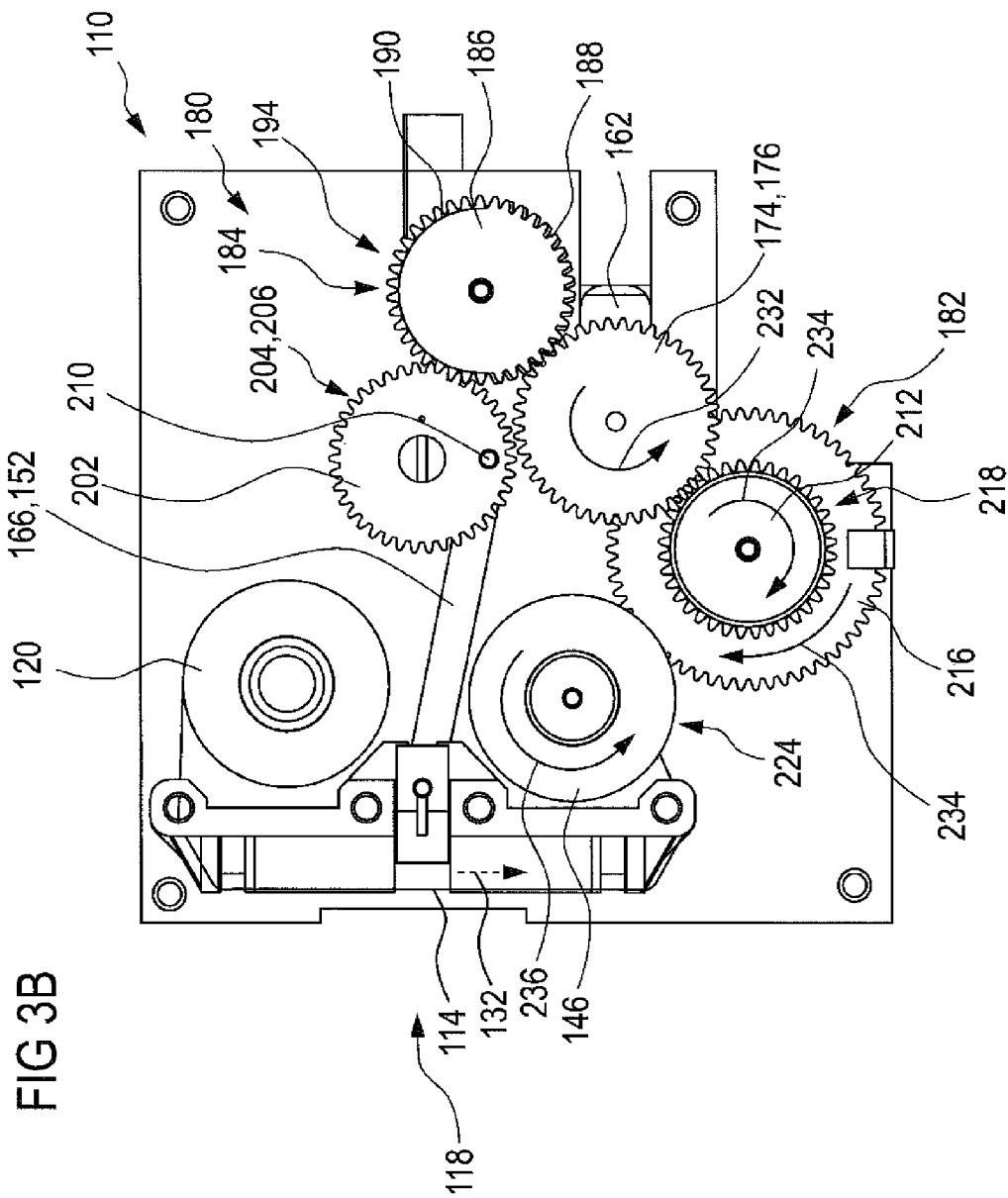

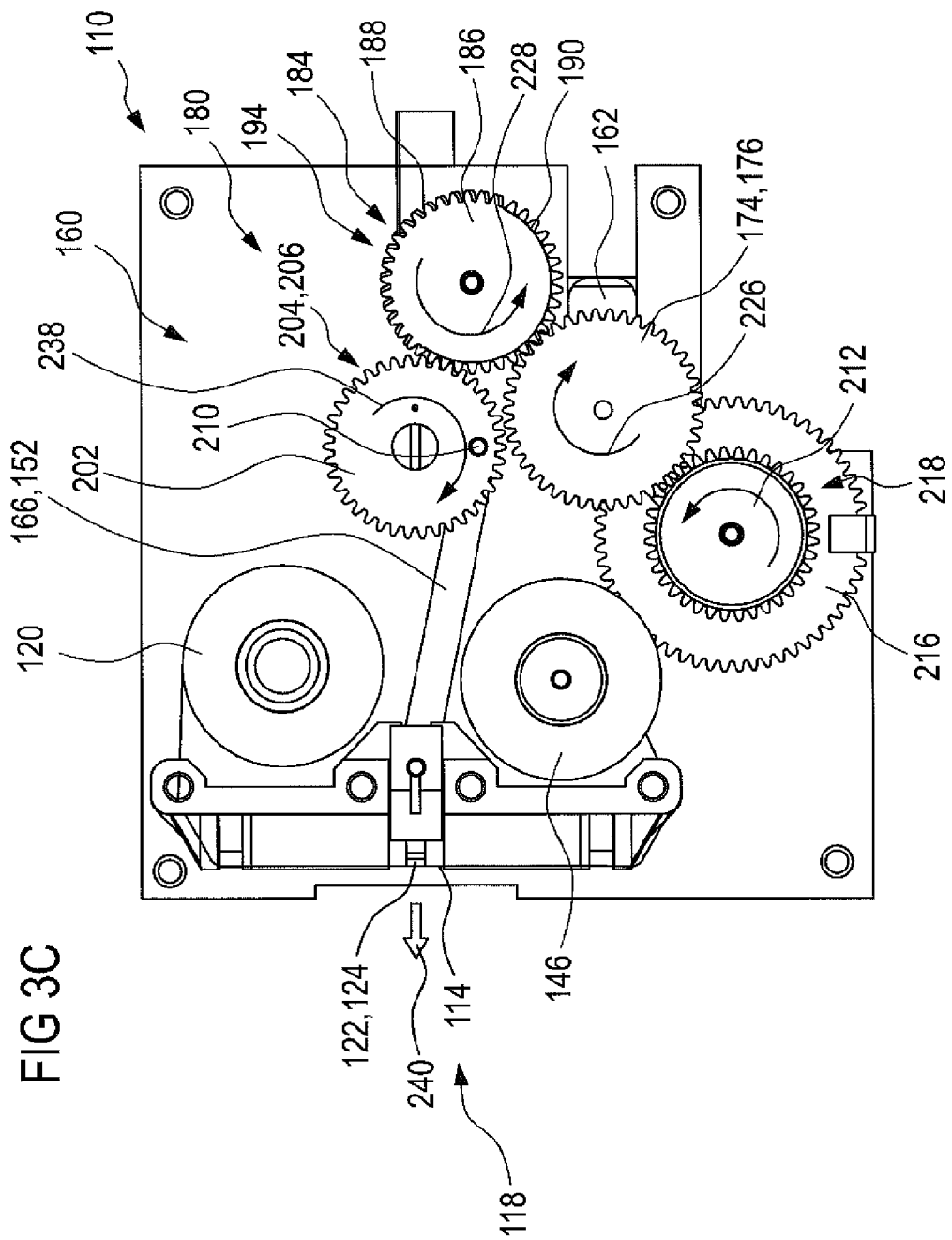

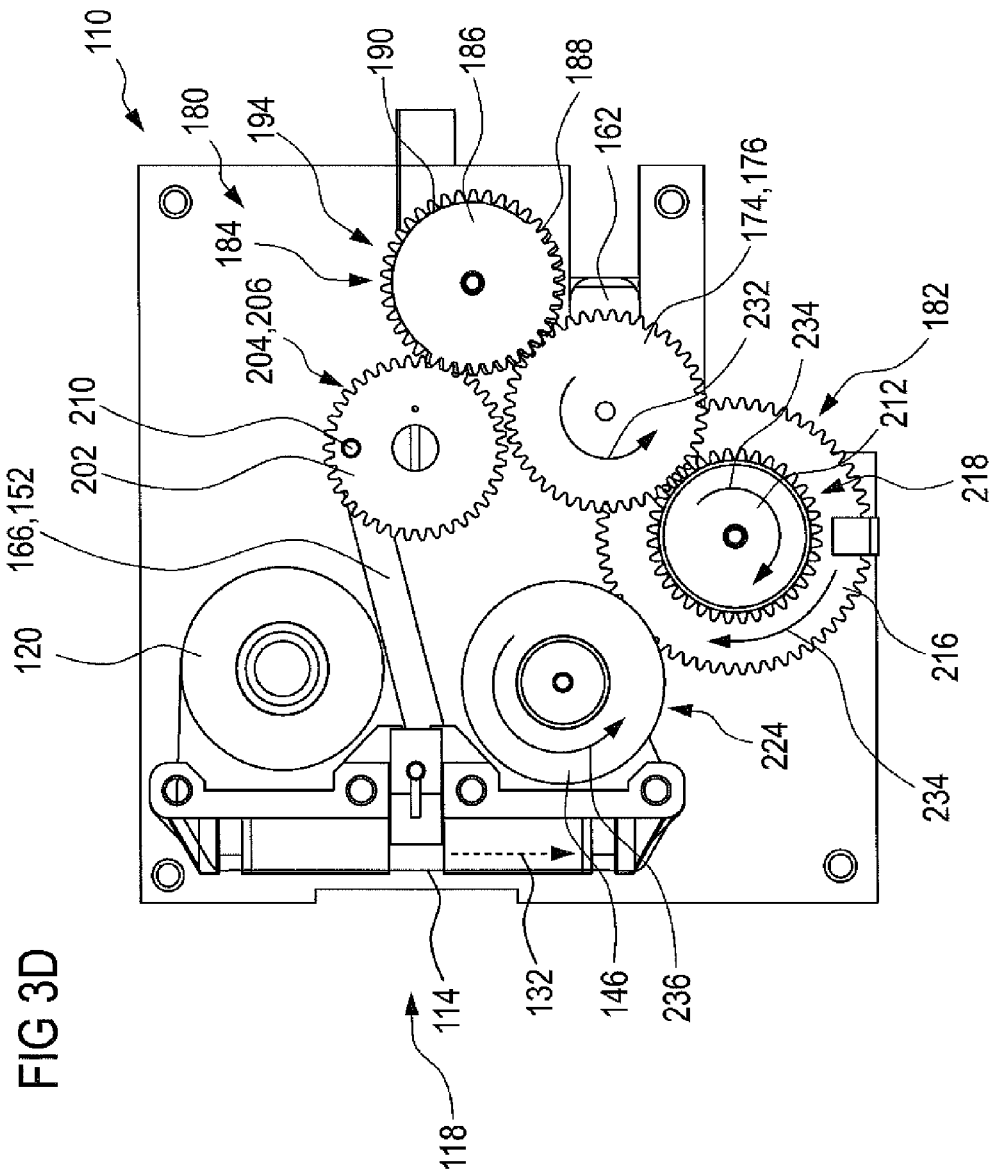

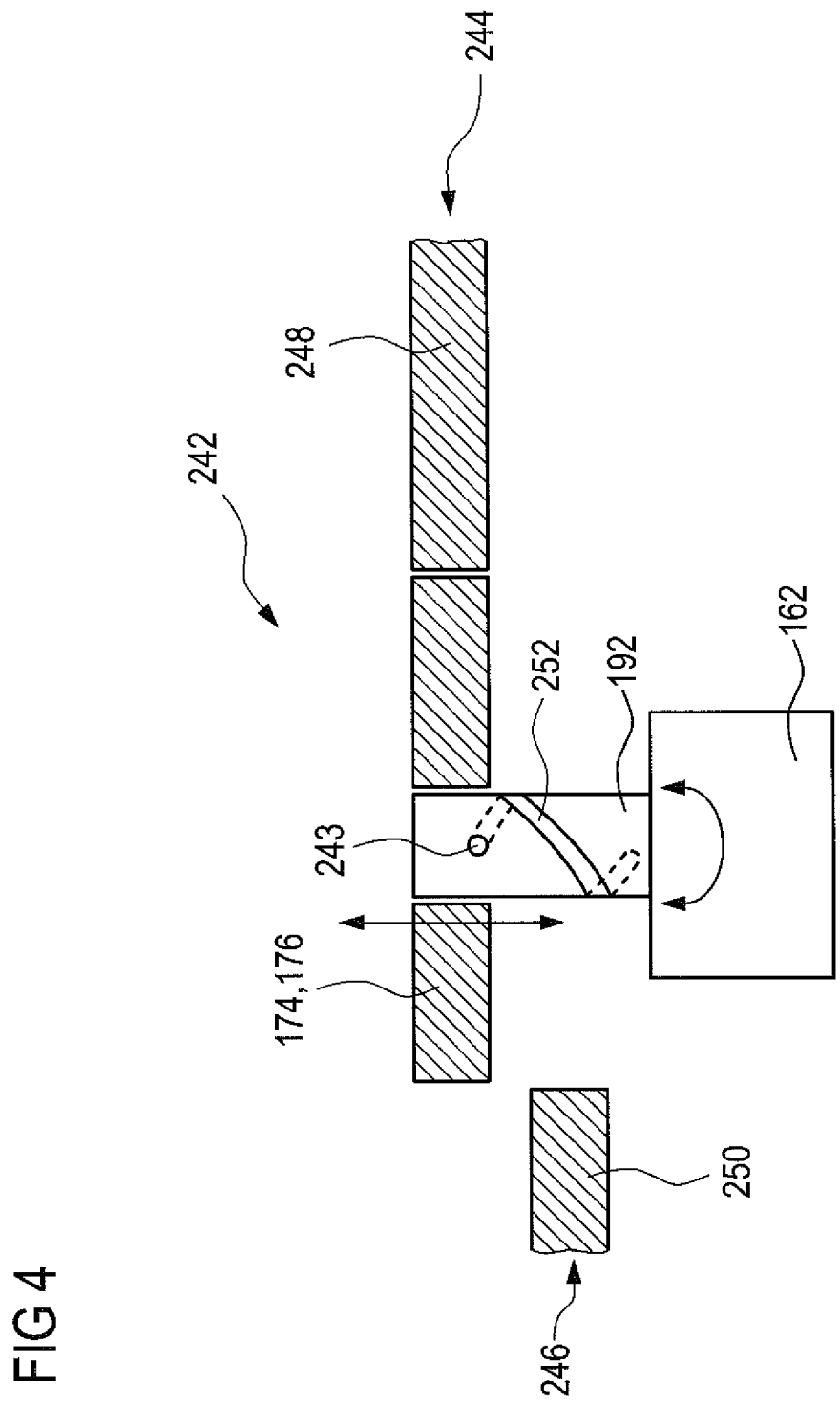

000
COMBINATION DRIVE FOR A SAMPLING SYSTEM FOR COLLECTING A LIQUID SAMPLE

RELATED APPLICATIONS

This is a continuation application of International Patent Application Serial Number PCT/EP2008/062547, filed Sep. 19, 2008, which claims priority to EP 07116748.0, filed Sep. 19, 2007, which are hereby incorporated by reference in their entirety.

BACKGROUND

The invention relates to a sampling system for collecting a liquid sample using at least one analytic auxiliary means. The invention further relates to a method for collecting a liquid sample. Such sampling systems and methods are used in particular in medical diagnostics in the hospital sector, in the home care sector or in a home-monitoring environment for determining the concentration of at least one analyte, for example, a metabolite such as blood glucose, in a bodily fluid.

Examining blood samples or other samples of bodily fluid, such as interstitial fluid, allows early and reliable detection of pathological states and the targeted and informed monitoring of body states in clinical diagnostics. Medical diagnostics generally require the collection of a sample of blood or interstitial fluid of the individual to be examined.

In order to obtain the sample, the skin, e.g., on the fingertips or ear lobe of the person to be examined, can be perforated using a sterile, pointed or sharp lancet so as to obtain a few microliters or less of blood for the analysis. This method is particularly suitable for the analysis of a sample which is performed directly after collecting the sample.

Lancets and so-called lancing devices which allow reproducible sample collection involving as little pain as possible are offered in particular in the sector of so-called "home monitoring," that is to say where laymen themselves perform simple analyses of the blood or interstitial fluid, particularly for the periodic (a few times a day) collection of blood by diabetics for monitoring blood glucose concentration. Such lancets and equipment (lancing devices) are, for example, the subject matter of Publication No. WO 98/48695A1, U.S. Pat. No. 4,442,836, U.S. Pat. No. 5,554,166 or Publication No. WO 2006/013045A1.

These days, self-determination of blood sugar is a universally adopted method in diabetes monitoring. In the prior art, blood sugar equipment generally has analysis equipment into which a test element (test strip) is inserted. The test element is brought into contact with a drop of a sample which was previously collected from, for example, the fingertip using a lancing device.

Analysis equipment in which the sample to be analyzed is situated on a test field on a test element and, if need be, reacts with one or more reagents in the test field before it is analyzed, is often used for analyzing liquid samples, e.g., bodily fluids such as blood or urine. Optical, in particular photometric, and electrochemical evaluations of test elements are the most common methods for quickly determining the concentration of analytes in samples. Analysis systems with test elements for sample analysis are generally used in the field of analysis, environmental analysis and, particularly, in the field of medical diagnostics. Test elements evaluated by photometric or electrochemical means are particularly important in the field of blood glucose diagnostics from capillary blood.

There are different forms of test elements. By way of example, basically square slides, which have a multilayered test field situated in the center thereof are known. Diagnostic test elements with a strip-shaped design are referred to as test strips. The prior art comprehensively describes test elements, for example, in the documents Canadian Patent No. 2311496 A1; U.S. Pat. No. 5,846,837; U.S. Pat. No. 6,036,919 or Publication No. WO 97/02487.

Analysis tapes with a plurality of test fields which are wound up in a cassette and provided for use in analysis equipment are examples of multilayered test elements disclosed in the prior art. By way of example, German Patent No. DE 103 32 488 A1, German Patent No. DE 103 43 896 A1, European Patent No. EP 1 424 040 A1, Publication No. WO 2004/056269 A1 and U.S. Publication No. 2006/0002816 A1 describe such cassettes and analysis tapes.

The numerous system components (lancet, lancing device, test element and analysis equipment) require a lot of space and are relatively complicated to handle. Systems with a higher degree of integration and thus simpler handling are also available in which the test elements are, for example, stored in a cartridge in the analysis equipment and provided for measurement. A further step in miniaturization can be achieved, for example, by integrating several functions or functional elements in a single analytic auxiliary means (disposable). By suitably combining a piercing process and sensory analyte concentration detection on a test element, the operation can, for example, be drastically simplified.

U.S. Publication No. 2006/0155317 discloses a lancet device for generating puncture wounds in a skin surface, which device comprises an integrated test element in the form of a reference element with a lancet and a sample take-up unit. The test element is firstly fixedly coupled onto a coupling mechanism of the lancet device. In a first position of the coupling mechanism, the lancet of the test element is actuated using a coupling rod and a connecting rod, and a piercing movement is carried out. Subsequently, the entire coupling mechanism with the test element fixedly coupled thereto is moved into a second position by a pivot movement, in which second position an opening of a sample take-up channel of the test element is situated over the puncture site for taking up a liquid sample.

Publication No. WO 2005/107596 discloses a multiplicity of spaced apart lancets on a tape. According to one embodiment, the tape not only carries the lancets, but also a multiplicity of test elements, each of which is assigned to one of the lancets. Therefore, this is a tape with a multiplicity of analytic auxiliary means which are arranged in a spaced apart fashion and allow integration of piercing procedures and sample take-up procedures in one sampling system.

The overall size plays a prominent role in integrated measurement systems. An object of integrated systems has to be that of providing equipment which is not much larger than the conventional non-integrated systems. One approach in this direction consists of using combination drives in which a motion sequence takes over a number of functions. By way of example, Publication No. WO 2006/013045 discloses a system in which an electrically operated motor firstly provides energy for a mechanical energy store and also operates an additional system function, either at the same time or independently therefrom. By way of example, this system function can be a cartridge transport or a test element transport. In order to use the motor at subsequent times for different functions, a transmission and/or a coupling is proposed which actively couples the motor to or again decouples the motor from the corresponding system function which is desired at the time. Various coupling systems are proposed.

The device proposed in Publication No. WO 2006/013045 therefore represents a substantial step toward a higher degree of integration. However, not all options for integration have been exhausted in this case because, even in the system proposed in Publication No. WO 2006/013045, there are still additional system functions which generally have to be supplied with energy by separate drives. Furthermore, the active coupling elements proposed in Publication No. WO 2006/013045 for coupling the drive to different system functions are technically complex and, in certain circumstances, susceptible to faults.

SUMMARY

The present invention provides a sampling system, in particular, a sampling system, which is suitable for collecting a liquid sample, in particular, a bodily fluid, and which addresses or avoids the disadvantages of the known systems. In particular, the sampling system provides a high degree of integration and a simple combination drive which is not susceptible to faults, which can be used for different subsystems, or system functions, of the sampling system.

The sampling system in accordance with these teachings should be designed for collecting a liquid sample, e.g., a body fluid, in particular, for detecting an analyte, for example, for a qualitative and/or quantitative detection of blood glucose. Here, a "sampling system" should be understood to be a system which is designed to generate this liquid sample and/or to take up the liquid sample and/or at least in part to process the taken-up sample, i.e., to wholly or partly analyze it. In this respect, the meaning of the term "sampling system" should be construed quite broadly.

The sampling system comprises at least one analytic auxiliary means. This analytic auxiliary means (also referred to as "analyte auxiliary unit") can, for example, control the take-up of the sample, the generation of the sample, the analysis of the sample, a combination of these functions or similar tasks. In this case, it is particularly useful for the analytic auxiliary means to have at least one lancet and/or at least one test element with at least one test field for analyzing the liquid sample. By way of example, the lancet can be a lancet needle or a lancet with an element with a sharp edge which, for example, is suitable for perforating an area of skin at the tip of the finger and/or on the ear lobe. By way of example, the test element can be designed as per one of the above-described test elements and can, for example, comprise a test field for optical analyte detection and/or for electrochemical analyte detection, respectively using suitable test chemicals.

In the process, a plurality of analytic auxiliary means or of one analytic auxiliary means which comprises a plurality of subunits of analytic auxiliary means (for example, a plurality of lancets and/or a plurality of test elements) can be provided. By way of example, the sampling system for taking up and providing a plurality of analytic test elements can comprise suitable elements, for example, a cartridge, in particular, a drum cartridge, a rod cartridge, a row cartridge or staggered cartridge, an analysis tape with a multiplicity of analytic auxiliary means, an analysis disk, on which a plurality of analytic auxiliary means are arranged, or similar elements which allow the provision and use of a multiplicity of these analytic auxiliary means. The analytic auxiliary means may include an analysis tape with a multiplicity of lancets and/or test fields being arranged on said analysis tape. Here, the lancets and test fields can be arranged alternately and so, for example, a subsequent test field may be assigned to each lancet. Tapes which only have lancets and tapes which only have test fields can also be used within the scope of the invention. Analysis tapes with lancets arranged thereon are also known as "lancet on tape" (LOT) analysis tapes. Here, the term "tape" in conjunction with "analysis tape" should preferably be understood to the effect that this analysis tape comprises a continuous carrier strip, for example, a carrier strip made of a polymer material (e.g., a polyester foil), a paper material or a composite material. However, the term "tape" is not limited to continuous tapes but in principle comprises any serial connection technique of adjoining analytic auxiliary means, such as lancets and/or test elements, which technique contains a serial supply of these analytic auxiliary means into an application position. Thus, for example, this term also comprises element chains, hook and eye connections, connections via intermediate elements or similar types of serial connections between adjoining analytic auxiliary means. Furthermore, reference is made to the fact that the invention, however, is not restricted to the use of analysis tapes but that, for example, different methods for providing analytic auxiliary means can also be used.

The sampling system comprises a coupling element for coupling onto the analytic auxiliary means and at least one drive unit for driving a movement of the coupling element from a rest position into a deflected position. In the process, the coupling may be performed such that, after the analytic auxiliary means (e.g., a lancet) has been used, it is in turn decoupled therefrom and so subsequently a next analytic auxiliary means can again be coupled, for example, a test element, for example, a test element arranged on the same analysis tape as the lancet used previously.

Hence, coupling to or coupling onto can in particular be understood to mean the generation of physical contact, and decoupling can be understood as the release or separation of this contact. The coupling element can actively and/or passively couple onto the analytic auxiliary means in the application position and can thus cause this analytic auxiliary means to likewise perform a movement along a defined path into one or more deflected positions. In the process, different deflected positions can be provided for different types of analytic auxiliary means, for example, a deflected position for taking up a sample using a test element and a deflected position for a piercing movement of a lancet.

Herein, an "active" coupling can be understood to mean different ways of coupling the coupling element to the analytic auxiliary means. Thus, for example, the coupling element can actively grip the analytic auxiliary means, for example, by using a gripper and/or a differently designed opening or closing mechanism which allows active coupling and decoupling. By contrast, in this context, a passive coupling is understood to be a coupling without active opening or closing, that is to say, for example, a simple exertion of a force by the coupling element onto the analytic auxiliary means or a coupling using barbed hooks.

An active or a passive coupling can also be understood in a different sense, with both possibilities being implementable in turn, namely, in the sense of an active or passive drive of the analytic auxiliary means by the coupling element. Here, an active coupling can be understood to mean a coupling in which the coupling element couples onto the analytic auxiliary means (for example, by a force-fit and/or interlocking coupling, for example, by gripping the lancet or the test element or as a result of a microstructure with barbed hooks which also pull back the lancet or the test element when the coupling element is pulled back) such that the return movement of the lancet or the test element from the deflected position into the rest position is also guided and driven by the coupling element. By contrast, in a passive coupling, the coupling element pushes or thrusts the analytic auxiliary means, e.g., the lancet or the test element, into the deflected position. The return movement of the analytic auxiliary means into the rest position then has to be performed by an additional drive element, for example, by a spring which is tensioned during the deflection of the lancet or the test element and which acts on the lancet or the test element when it relaxes and so there is a return movement of the lancet or the test element into the rest position.

The coupling element can be coupled onto the analytic auxiliary means in different ways which can, for example, be matched to the embodiment of the analytic auxiliary means. In the process, any drive which is suitable for bringing about a defined travel of the analytic auxiliary means can be used in principle. Here, eccentric drives, toggle link drives or the like can be mentioned as examples. However, the coupling element can comprise a connecting rod drive and/or a crank drive, particularly if use is made of an analysis tape. The connecting rod drive can, for example, comprise a connecting rod. The connecting rod drive and/or the crank drive should be designed such that they couple onto an analytic auxiliary means arranged in an application position. Within the scope of the present invention, an "application position" is intended to be understood as a position in which the analytic auxiliary means can be used for a sampling function of the sampling system. By way of example, this can be a position in which a lancet performs a piercing movement for perforating an area of skin and/or a position in which a test element is used for collecting or taking up a liquid sample. In both cases, the analytic auxiliary means (that is to say the lancet in one case and the test element in the other case) is deflected from its rest position in order to perform the described function. If different types of analytic auxiliary means are provided, such as a lancet and a test element, provision can also be made of a plurality of application positions for these different types of analytic auxiliary means. However, one and the same application position can be used for all analytic auxiliary means. By way of example, the application position can comprise an opening in a housing of the sampling system, for example, an opening which can be closed off by a flap or a slider.

The drive unit which drives the movement of the coupling element comprises an energy transducer. This energy transducer can be designed as an electromechanical energy transducer. Within the scope of the present invention, an "electromechanical energy transducer" is intended to be understood to be a transducer which converts electrical energy, for example, electrical energy provided by an electrical energy supply (e.g., a power cable) and/or an electrical energy store (e.g., an accumulator, a battery or a capacitor), into mechanical energy. In the process, the use of an electric motor is within the scope of the present invention. However, alternatively or additionally, the energy transducer can also comprise different types of electromechanical energy transducers, for example, actuators, pumps or similar transducers or transducer combinations. However, in principle, any other type of energy transducer would also be feasible instead of the electrical-mechanical (i.e., electromechanical) energy transducer, that is to say a transducer which is designed to convert one type of energy into mechanical energy, e.g., rotational energy. By way of example, a mechanically actuated drive, that is to say a mechanical-mechanical energy transducer, would be possible. In this respect, the term "energy transducer" should be taken quite broadly and should in principle comprise any type of drive in which one type of energy (e.g., electrical and/or mechanical energy) is converted into movement energy.

The energy transducer is designed to generate a rotational movement which contains different rotational directions. If an electric motor is used, this can, for example, be performed by a simple pole reversal which leads to a reversal in the rotational direction.

A basic idea of these teachings consists of increasing the degree of integration of the sampling system by using these differing rotational directions of the energy transducer for different system functions. For this purpose, the drive unit furthermore comprises a coupling device which can couple onto the energy transducer and can supply mechanical energy, in particular, rotational energy, provided by the latter to different system functions. For this purpose, the coupling device has at least one rotational-direction sensitive element and is designed to couple the energy transducer onto at least a first system function in a first rotational direction, and to couple said transducer onto at least a second system function which differs from the first system function in a second rotational direction which differs from the first rotational direction. Thus, it is possible to switch between different system functions using the rotational-direction sensitive element.

Coupling or decoupling a system function should in this case be understood to mean an action of the sampling system in which the respective system function is activated and used, or deactivated and no longer used. The first and/or the second system function can be a multiplicity of possible functions of the sampling system or a combination of such functions. In the process, the first system function and/or the second system function can comprise at least one of the following functions of the sampling system: a drive for a piercing movement of a lancet of the analytic auxiliary means; a sampling movement of a test element of the analytic auxiliary means; a tensioning of an energy store for driving the piercing movement of a lancet, in particular a mechanical energy store (e.g., a spring element), a transport function of an analytic auxiliary means for providing the analytic auxiliary means in an application position, a transport function of an analytic auxiliary means for providing the analytic auxiliary means (in particular a test element of the analytic auxiliary means) in a measurement position, in particular a measurement position for optical and/or electrochemical evaluation of the test element, a transport function of a cartridge of the sampling system for providing in an application position an analytic auxiliary means from a cartridge (e.g., advancing a cartridge), a transport function of an analysis tape containing a plurality of analytic auxiliary means for providing an analytic auxiliary means in an application position (e.g., advancing the analysis tape for providing a test element and/or advancing said tape for providing a lancet), a transport function of an analysis disk containing a plurality of analytic auxiliary means for providing an analytic auxiliary means in an application position. However, alternatively or additionally, further system functions can also be used. In the process, it is also possible for a cycle to be used in which the rotational direction is changed repeatedly in different phases within the scope of a single cycle, with wholly or partly different system functions being coupled on in each case. By way of example, a cycle can comprise four phases:

first phase: rotation in the first rotational direction, coupling to system function A,
second phase: rotation in the second rotational direction, coupling to system function B,
third phase: rotation in the first rotational direction, coupling to system function C, and
fourth phase: rotation in the second rotational direction, coupling to system function D.

However, other refinements are also feasible, for example, cycles with more or fewer than four phases and/or the coupling of multiple system functions in one phase and/or the repetition of the coupling of a system function in different phases (that is to say, for example, that system functions A and C are identical in the above example).

The at least one first system function and the at least one second system function can in this case respectively comprise one or more system functions. If provision is made of a plurality of first and/or second system functions, these can, for example, be carried out simultaneously, overlapping in time or offset in time. By way of example, this can be performed by virtue of the fact that system functions are coupled at different angular positions in the same rotational direction of the energy transducer which, as will be explained in more detail below on the basis of examples, can, for example, be effected by partly toothed gearwheels or similar coupling mechanisms. A time offset in coupling to a plurality of system functions in the same rotational direction can also be performed in a different fashion. One example of a time-offset coupling of a plurality of system functions to a rotation in the same direction is a tensioning or charging of an energy store, followed by a release procedure. Further examples will be explained in more detail below.

The proposed sampling system, in which two different rotational directions of the energy transducer are used in order to activate different system functions or to supply the latter with energy, offers a number of advantages, particularly in respect of the system complexity and system reliability, over conventional integrated sampling systems, for example, the systems described above which are disclosed in the prior art. Thus, the degree of integration in particular is significantly increased as result of using both rotational directions. Additionally, active coupling and decoupling of individual system functions, as carried out by, for example, the coupling mechanisms described in Publication No. WO 2006/013045, is not mandatory. Thus, an independent coupling movement for coupling or decoupling the system functions, which requires an additional actuator, user intervention or the like, can be dispensed with. The different system functions can, for example, exclusively be activated or coupled as a result of the rotational direction of an electric motor or a differently designed energy transducer, which, for example, can be implemented easily by an electronic control of the sampling system. By way of example, the sampling system can comprise a control for this purpose, for example, a microcomputer and/or another type of electronic control, which couples the different system functions by prescribing the rotational direction of the energy transducer. This affords the possibility of easily controlling individual phases or cycles of the operation of the sampling system without additional actuation of coupling elements being necessary.

The sampling system can be advantageously developed in different ways, with it being possible for the developments to depend on, in particular, the functionality of the sampling system. By way of example, if the sampling system comprises a lancet for perforating an area of skin, it is particularly suitable for the sampling system to furthermore comprise a mechanical energy store. This mechanical energy store should be designed to emit energy for a piercing movement of a lancet of the analytic auxiliary means, which energy is in turn transmitted to the lancet via the coupling element. This coupling can be designed such that the lancet achieves a velocity of approximately 2 to 3 m/s during the piercing movement and so an energy store which is able to quickly release the stored energy can be used as a mechanical energy store. For this purpose, energy stores comprising a spring element, for example, a helical spring, a spiral spring, a leaf spring, a cup spring or another type of spring element, have proven to be particularly advantageous. However, the mechanical energy store can furthermore, alternatively or additionally, also comprise an elastic element, for example, an elastomeric element (e.g., a rubber element) which can be tensioned by compression and/or stretching such that mechanical energy is stored. However, other types of energy stores can also be used, for example, pneumatic pressure stores or other types of store.

If such a mechanical energy store is used, the sampling system should in particular have a device which allows an abrupt release of the stored mechanical energy and a transmission to the lancet. In the process, a multiplicity of release mechanisms may in principle be used, for example, release mechanisms which comprise a mechanical switch for the release. By way of example, this switch can by activated by a user action or, alternatively or additionally, once again via an electronic control of the sampling system. However, it is envisioned that for exemplary embodiments that the release of the lancet movement, that is to say a release of the energy of the mechanical energy store to the lancet, is also carried out via the drive unit, particularly, via a rotational movement of the energy transducer. For this purpose, the drive unit can, for example, have a toothed transmission, wherein the toothed transmission is designed to charge the mechanical energy store in a first angular position range of the energy transducer and to keep said store in a charged state, wherein the toothed transmission is furthermore designed to release the mechanical energy store in a second angular position range and so energy is provided for the piercing movement of the lancet. For this purpose, the toothed transmission can, for example, have one or more partly toothed gearwheels, with the partly toothed gearwheel being toothed in at least a first circumferential region and not being toothed in at least a second circumferential region. However, the term "gearwheel" should be construed broadly in this context and it comprises a multiplicity of possible gearwheel systems such as spur gear gearwheels, bevel gear gearwheels, worm gearwheels, rack-and-pinion gearwheels, spindle gearwheels, contrate gearwheels, planetary gearwheels or the like. Additionally, the toothed transmission can also have a lock, with the lock being designed to prevent an undesired discharge of the energy store in the first angular position range. By way of example, this lock can comprise a catch which prevents the discharge of the energy store in the first angular position range. However, other types of lock can also be implemented.

Overall, the entire drive unit can comprise a gearwheel system, with it being possible for the abovementioned gearwheel systems to be used individually or in combination. Thus, the gearwheel system can in turn comprise, for example, one or more of the following transmission elements: a spur gear transmission, a bevel gear transmission, a worm gear transmission, a rack-and-pinion gear transmission, a spindle gear transmission, a contrate gear transmission, a planetary gear transmission. In the process, the gearwheel system can be arranged in a plane, however it is also possible for individual elements or a number of elements of the gearwheel transmission to project out of this plane, for example, within the scope of a bevel gear transmission. The plane of the gearwheel transmission can then also be the plane in which the movement of the analytic auxiliary means into the deflected position is carried out, for example, the sampling movement or sample take-up movement of the test element and/or the lancet movement of the lancet. As a result of this, the overall sampling system can have a particularly flat design. However, other embodiments are also feasible, for example, a lancet movement and/or a sampling movement which is perpendicular to a plane of the gearwheel transmission.

In a particular embodiment, the coupling device comprises a first drive wheel and a second drive element. This first drive wheel can again, for example, be one of the above-described gearwheels and/or a combination of such gearwheels. The second drive element can also be designed as a wheel, but a drive rod can also be provided in this case. Again, one or more of the above-described toothed transmissions can be used.

The first drive wheel is coupled to the energy transducer. This coupling can be performed directly or indirectly, i.e., via an intermediate transmission or intermediate coupling, such that the first drive wheel can be driven by the energy transducer, in both directions. The second drive element is coupled to the first system function and/or the second system function. The first drive wheel and the second drive element are interconnected by the rotational-direction sensitive element. Here, this rotational-direction sensitive element is designed such that it couples together the first drive wheel and the second drive element in a first rotational direction (e.g., clockwise or counterclockwise) and decouples the first drive wheel and the second drive element from one another in a second rotational direction (e.g., counterclockwise or clockwise). As a result of this development, a system function can be coupled or decoupled by simple setting of a certain rotational direction and by using the first drive wheel, the second drive element and the rotational-direction sensitive element.

In the process, it is particularly useful for provision to be made of two or even more second drive elements which are connected to the first drive wheel by two or more rotational-direction sensitive elements. In the process, the respective rotational-direction sensitive elements should be designed such that the first drive wheel is respectively coupled to different drive elements in different rotational directions. Thus, for example, the first drive wheel can couple onto a first of the second drive elements in a first rotational direction and to a second of the second drive elements in a second rotational direction. This affords the possibility of respectively coupling different system functions onto the first drive wheel, which system functions can be activated depending on the rotational direction. "Rotational-direction sensitivity" of the rotational-direction sensitive element should in this case be understood to mean the direction in which the coupling between the first drive wheel and the second drive element is effected, or the direction in which there is decoupling. These directions should in each case be different for the two or more second drive elements.

A further advantageous development relates to an embodiment of the rotational-direction sensitive element. Thus, it is particularly advantageous for this rotational-direction sensitive element to have at least one freewheel. In this case, a freewheel should be understood to be a rotational coupling between two elements which in one rotational direction of a first of these elements effects a force-fit or interlocking coupling to the second element (and thus driving), with this force-fit or interlocking being lifted in the other rotational direction. Such freewheels are also referred to as overrunning couplings.

Very different embodiments of freewheels are known from the prior art. Here, it is within the scope of these teachings for the freewheel to comprise a clamping roller freewheel (wherein "rollers" can be understood here as both rollers and balls), a clamping body freewheel, a catch freewheel, a frictional-locking mechanism freewheel, a finger freewheel or a combination of these and/or other types of freewheels. So as to reduce the problem of freewheel dead travel, i.e., the rotational range in the driving direction in which there is no driving even in this driving direction, which is known in conventional freewheels, the freewheel can furthermore comprise at least one freewheel lock. Such freewheel locks which reduce the freewheel dead travel are known from the prior art.

However, as an alternative to, or in addition to, the described use of a freewheel, the rotational-direction sensitive element can be also designed in a different fashion or can comprise different types of rotational-direction sensitive elements. Such other embodiments of rotational-direction sensitive elements, for example, comprise couplings on different planes, with one plane being used for each rotational direction. Thus, by way of example, the rotational-direction sensitive element can have at least one first drive wheel coupled to the energy transducer and at least two second drive elements coupled to different system functions and arranged in different planes. With respect to the term "drive elements", reference is once again made to the options described above. Here, the first drive wheel is designed such that, in the first rotational direction, it is arranged on a first plane and coupled to a first of the second drive elements, and that, in the second rotational direction, the first drive wheel is arranged on a second plane and coupled to a second of the second drive elements. This use of different planes can, for example, be effected by the first drive wheel being arranged on an axle in which a groove or a thread is provided, with an engagement element (e.g., a thread section, a toothed section, a pin, a bolt or a spur) of the first drive wheel engaging therein. The first drive wheel is then "screwed" onto the first plane in a first rotational direction, whereas the drive wheel is moved (screwed) onto the second plane in the second rotational direction. Other types of movement to the different planes are also feasible. This option also constitutes an implementation of the inventive idea that different rotational directions of the energy transducer can be used for coupling to different system functions.

Different system functions can also be coupled to one another in one and the same rotational direction. Thus, for example, the sampling system can be designed such that two or more system functions are coupled to the energy transducer in the first rotational direction or, alternatively or additionally, at least two different system functions are also coupled to the energy transducer in the second rotational direction.

Within the scope of this development, in one of the rotational directions (i.e., in the first or the second rotational direction), there simultaneously can be a coupling to the energy transducer of the system function in which a mechanical energy store is charged with energy and of a system function in which a test element is transferred into a deflected position in which a liquid sample can be applied to a test field on the test element. This coupling of charging the energy store and a sampling movement is particularly useful because both system functions generally require a slow movement. Thus, a sampling movement using a test element, for example, for collecting a drop of blood using a test field arranged on a tape, is performed by a movement which is usually carried out at a velocity of a few cm/s.

If one rotational direction is used in a combined fashion for charging the energy store and for a sampling movement, it is useful for the coupling device to be arranged such that the energy transducer can, in the second rotational direction which differs from the first rotational direction, be coupled to a system function in which an analytic auxiliary means is provided in an application position.

If the same drive unit with the coupling device is used for coupling onto different system functions, there often is the technical challenge of these system functions requiring a different kind of provision of drive energy. Thus, for example, a force to be provided, a torque to be provided, an amount of energy to be provided, a duration of the coupling or other variables may vary, depending on the system function. Even within one and the same system function, the optimum coupling or the optimum provision of one or more of the mentioned and/or other variables can change over the period of use of the sampling system. A typical example of such a change generally occurs when transport functions of the sampling system are intended to be coupled. Examples are transport functions of one or more tapes, e.g., analysis tapes, which contain a plurality of analytic auxiliary means, for example, a plurality of lancets and/or test elements or test fields. Such tapes can, for example, be provided by reels and/or coils. However, with increasing winding or unwinding of such a coil, e.g., a supply reel and/or a take-up reel, the coil conditions change because the distance of the unwinding position of the tape from the rotational axis increases or decreases. Thus, for example, the unwinding point has an increased distance from the rotational axis in the case of a large number of windings on a coil compared to a lower number of windings. Therefore, if the tape is intended to be spooled by a predetermined distance then, compared to a lower number of windings, all that is required is a smaller rotational angle because the rotational angle or coil angle is inversely proportional to the distance from the rotational axis. In order to nevertheless always position an analytic auxiliary means precisely in an application position and/or measurement position, additional technical measures, which ensure constancy of the coupling onto the respective system function, even over a period of operation of the sampling system, are therefore desirable.

Therefore, in one embodiment, the sampling system, particularly the at least one drive unit, has at least one slip coupling. Within the scope of the present invention, a slip coupling should be understood to be an element which switches independently on the basis of the torque to be transmitted and/or on the basis of the force to be transmitted. Thus, the slip coupling may, for example, have a maximum force and/or a maximum torque, with coupling being prevented independently if the force required or the torque required for coupling onto the system function exceeds the maximum force and/or the maximum torque. Alternatively, there can also be independent switching in the opposite direction such that there is coupling above the maximum force or the maximum torque, but not therebelow.

Such slip couplings are known in a number of different embodiments. Thus, the at least one slip coupling can, for example, comprise at least one of the following types of slip coupling: a force-fit coupling, in particular, a slip coupling with a friction coupling; an interlocking slip coupling, in particular, a slip coupling with at least one spring-loaded first engagement element which decouples from engagement with at least one second engagement element when a maximum force and/or a maximum torque is reached; a slip coupling with a spiral spring; a slip coupling with a spring arm; a slip coupling with a flexible plastics and/or metal element. Different exemplary embodiments of such slip couplings are explained in more detail below.

Slip couplings are often also referred to as safety couplings or overload couplings. In the process, the maximum torque and/or the maximum force do not have to correspond to a precisely defined value, but there can also be a continuous and/or stepwise transition between coupling and decoupling of the slip coupling.

As illustrated above, the slip coupling can be provided at different sites within the sampling system and/or the drive unit and/or the coupling device. The use of a plurality of slip couplings is also feasible. The sampling system can comprise one or more slip couplings, wholly or partly at different sites.

The drive unit can comprise at least one slip coupling. However, alternatively or additionally, provision can also be made of one or more slip couplings at other sites in the sampling system. In the process, the sampling system, particularly the drive unit, can wholly or partly comprise the slip coupling. Thus, the drive unit can also, for example, merely partly comprise the slip coupling instead of completely comprising the slip coupling. Therefore, for example, merely one part of the slip coupling can be integrated into the drive unit while a second part of the slip coupling can be comprised in another element of the sampling system, for example, in an element which provides the system function to which the coupling is intended to be effected.

As illustrated above, the problem of changing the coupling parameters, for example, the force to be provided, the torque to be provided, energy to be provided, a duration of the coupling, a distance of the coupling or similar parameters or combinations of the mentioned or other coupling parameters, occurs particularly when the system function to which the coupling is intended to be effected comprises at least one transport function. Thus, the first system function and/or the second system function can, for example, comprise at least one of the following functions of the sampling system: a transport function of an analytic auxiliary means for providing in a measurement position the analytic auxiliary means; a transport function of a cartridge of the sampling system for providing in an application position an analytic auxiliary means from a cartridge; a transport function of an analysis tape containing a plurality of analytic auxiliary means for providing in an application position an analytic auxiliary means; a transport function of an analysis disk containing a plurality of analytic auxiliary means for providing in an application position an analytic auxiliary means. In this case, the slip coupling can be designed to suppress or prevent further execution of the transport function when a position in the measurement position and/or application position has been reached. By way of example, this can be performed by a further execution of the transport function requiring the provision of a torque and/or a force by the drive unit or coupling unit which would exceed the maximum force and/or the maximum torque. By way of example, this can be carried out by the sampling system furthermore comprising at least one blocking element, with the blocking element being designed to generate a locking force and/or a locking torque in the measurement position and/or application position, which force and/or torque exceeds a maximum force and/or a maximum torque of the slip coupling. This can prevent the transport function from being executed any further.

Such a blocking element can be produced in a number of ways. Thus, these blocking elements can, for example, comprise holes, for example, one or more holes in a tape, for example, an analysis tape with one or more test elements and/or one or more lancets. A lock of the blocking element can engage into these holes in order to prevent onward transport of the tape. The blocking elements can, for example, also be designed as steps running transversely to a longitudinal direction of the tape, which steps butt against a stop of the sampling system as soon as an analytic auxiliary means, for example, a lancet and/or a test element, has reached a measurement position and/or an application position. The blocking element then exerts a counteracting force and/or a counteracting torque which exceed or exceeds the maximum force and/or the maximum torque of the slip coupling and so there is a decoupling from the transport function and an onward transport is prevented. Thereupon the slip coupling slips through.

Alternatively or additionally, a number of further types of blocking elements are feasible and can be implemented. Thus, for example, a counteracting force and/or a counteracting torque can also be applied by the provision on the analysis tape of sites with varying dimensions, in particular with varying thicknesses, which sites are arranged in a defined fashion and interact with a corresponding mechanism of the sampling system. Once these sites, e.g., swellings, have reached a certain position, the mechanism can recognize this, e.g., by scanning, and the desired counteracting torque and/or the desired counteracting force can, e.g., automatically, be transferred onto the analysis tape. An example of such sites on the analysis tape with a geometry which deviates from the remaining analysis tape can be test elements, test fields or lancets, which can, for example, cause a change in the thickness of the analysis tape at the respective point as a result of their spatial extent. Thus, by way of example, the blocking element can comprise a mechanism which has a gripper, in particular a permanently closed gripper. This gripper can then, for example, scan the thickness of the analysis tape. Thus, by way of example, provision can be made of a gripper, in particular, a spring-loaded gripper, through which the analysis tape is pulled with almost no friction. If the site with a deviating thickness, for example, the swelling of a certain lancet to be used, butts against an edge of the gripper provided for this purpose, a counteracting force is exerted on the analysis tape and is converted into a counteracting torque in a reel, for example, a take-up reel. Subsequently, in a further method step, the blocking element can again be released to allow onward transport of the analysis tape. By way of example, the gripper can briefly be opened automatically or manually for this purpose or can be released in another way. However, as an alternative to, or in addition to, the described blocking element, other types of blocking elements are also feasible for generating a counteracting force and/or a counteracting torque.

In particular, the use of a blocking element is advantageous in that the drive movement does not have to be matched to the supply path required for the correct positioning in the application position and/or in the measurement position and can therefore also be larger. A change of the required supply path, for example, as a result of the above-described unwinding effect and/or winding effect, can also be prevented as a result of this.

The at least one analytic auxiliary means may comprise at least one analysis tape with at least one test element, for example, a test element with at least one test field, and/or at least one lancet. By way of example, this can be an analysis tape with a plurality of test fields arranged in a winding direction, a plurality of lancets arranged in a winding direction and/or with a plurality of alternately arranged test fields and lancets. Such an analysis tape can, for example, be held on one or more coils and/or reels which can, for example, be part of a tape cassette described in more detail below. By way of example, there can be at least one supply reel, which contains test elements and/or lancets which are sill unused, and/or at least one take-up reel, which can contain used test elements and/or lancets. In this case, the described transport function can, for example, comprise a drive of the supply reel and/or the take-up reel. By way of example, the take-up reel can be driven by a reel drive, for example, a reel drive gearwheel which is part of the drive unit. The coupling between reel drive and reel, e.g., take-up reel, can then, for example, be performed by means of the at least one slip coupling described above.

Overall, as a result of the use of the at least one slip coupling, a stable and smooth operation of the sampling system can be implemented in a technically simple fashion. The coupling onto different system functions, in which the coupling parameters can change, can be significantly improved and simplified as a result of this. However, in general, reference is made to the fact that the previous embodiments, and the embodiments described in the following text, in which the sampling system comprises a slip coupling can also be used independently of the implementation of the remaining aspects of these teachings. Thus, in general, a sampling system for collecting a liquid sample, which has at least one analytic auxiliary means, can be equipped with a slip coupling in order to generally improve or smooth a coupling of the sampling system to the analytic auxiliary means usually designed as a consumable. Thus, for example, as described above, an arbitrary reel drive and/or another type of transport function, in which the analytic auxiliary means is transported and/or moved in a different fashion, can be performed using at least one slip coupling. A coupling of a drive unit onto different system functions is not mandatory in this case. However, the use of a slip coupling is, for the reasons described above, particularly advantageous for embodiments which contain coupling onto different system functions.

Reference is furthermore made to the fact that the use as outlined above of one or more slip couplings for coupling onto one, more or all system functions is not mandatory. The sampling system can also be implemented in its entirety without the mentioned slip coupling. Thus, for example, the sampling system and/or the drive unit can also wholly or partly be equipped with an electronic control which can control and/or carry out the coupling. By way of example, a slip coupling can be dispensed with in this case because the respectively required coupling parameters can, for example, be provided and/or set and/or controlled by the electronic control. However, even in the case of using at least one electronic control in the sampling system and/or in the drive unit, provision can in principle be made of one or more slip couplings in the sampling system and/or in the drive unit. However, the use of one or more slip couplings is particularly advantageous in, for example, the case of a purely mechanical drive unit and/or a purely mechanical coupling.

The above-described sampling system in one of the possible embodiments can be used, as already described above, within the scope of different operational phases performed in sequence which, in their entirety, form a sampling cycle. In the process, a sampling system and a method which comprise both the generation of a liquid sample (for example, a lancet movement) and a collection of the liquid sample using a test element can be provided. For this purpose, a method for collecting a liquid sample is proposed, which, for example, can be carried out on a sampling system as per one of the above embodiments, as well as a sampling system which is designed to carry out the proposed method or the sampling sequence. In the process, the method steps described in the following text can be performed in the sequence illustrated in the following text, however other method steps (not illustrated) can also be additionally performed. Alternatively, other sequences than the one illustrated below are also possible. Additionally, the illustrated sequence of method steps a) to d) can be permuted cyclically or anticyclically and so, instead of the sequence a), b), c), d), the sequences d), a), b), c); c), d), a), b) or b), c), d), a) can, for example, also be performed. Furthermore, it is also possible for individual or a number of method steps to be performed repeatedly or individual method steps can be performed in parallel or overlapping in time.

The method comprises the following steps:

a) The energy transducer performs a first rotational movement in the first rotational direction, wherein a mechanical energy store is released and emits energy for a piercing movement of a lancet of the analytic auxiliary means, which lancet is arranged in an application position.

b) The energy transducer performs a second rotational movement in the second rotational direction, wherein a test element with a test field for analyzing the liquid sample is transferred into the application position.

c) The energy transducer performs a third rotational movement in the first rotational direction, wherein the mechanical energy store is charged with energy and wherein the test element is transferred into a deflected position for applying a liquid sample to the test field on the test element.

d) The energy transducer performs a fourth rotational movement in the second rotational direction, wherein a lancet is transferred into the application position.

As described above, further method steps can be provided. Thus, for example, a measurement step can be provided between method steps c) and d) and/or at different times, in which measurement step the test element onto which the liquid sample was applied is evaluated, i.e., measured. This can, for example, be performed directly in the application position, and in this case a corresponding measurement apparatus (e.g., an optical and/or electrochemical measurement apparatus) would be provided in the application position. However, alternatively or additionally, the measurement can also be performed in another position, particularly in a specific measurement position. By way of example, for this purpose, provision can in this case be made of a separate transport step in which the test element with the sample applied thereon is transferred into the measurement position. By way of example, a corresponding measurement optical device or another type of measuring apparatus can be provided in this measurement position. However, in particular, the separate transport step can also be performed between method steps c) and d). The transport step can also wholly or partly coincide with other method steps, for example, with method step d). By way of example, the sampling system can in this case be designed such that the distance between a lancet and a test field on the test element corresponds exactly to the distance between the measurement position and the application position. If the lancet is driven into the application position in method step d), the test field is then also simultaneously driven into the measurement position. However, other refinements are also possible.

In one of the illustrated variants, the described method affords the possibility of performing, one after the other, or activating, different functions required for sampling in a very integrated fashion and with a single energy transducer. Additional method steps (not listed) can, for example, comprise the analysis of the liquid sample on the test field, for example, as described above, a quantitative detection of at least one analyte in the sample using test chemicals, using an optical method and/or using an electrochemical method. This detection can likewise be performed directly in the application position, for example, by the test element being irradiated by light in this application and by, for example, a color change being detected, or provision can be made of a separate analysis position in which the test element is evaluated.

In addition to the sampling system and the described method, in one of the illustrated embodiments a tape cassette is furthermore proposed, which cassette is suitable for use in a sampling system as per one of the exemplary embodiments described above. The tape cassette comprises an analysis tape as per the above description, that is to say in particular a tape on which at least one test element and/or at least one lancet are arranged. The tape cassette furthermore comprises at least one supply reel, from which the analysis tape can be unwound and provided, and at least one take-up reel, that is to say a roll onto which used analysis tape can be wound up. It is furthermore possible to integrate part of the coupling element into the tape cassette and thus to design it in an interchangeable fashion. This simplifies the coupling onto the analysis tape when the tape cassette is replaced because now it is only the part of the coupling element remaining in the tape cassette that has to be coupled onto the remaining, not replaced coupling element when the tape cassette is interchanged, but a new coupling onto the sensitive tape is not required. In particular, the coupling piece (which may directly interact with the analysis tape) can, for example, be designed as an interchangeable part of the tape cassette. In addition, the tape cassette can comprise further parts, for example, a housing, a base plate and further elements. In particular, the tape cassette can, as a result of its mechanical dimensions, be suitable for insertion or introduction into the sampling system, for example, into a housing of the sampling system, and can be designed as a single-use or multiple-use, i.e., recyclable, tape cassette.

BRIEF DESCRIPTION OF THE DRAWINGS

Further details and features of the invention emerge from the following description of exemplary embodiments. Herein, the respective features can be implemented individually or a number of features can be combined. The invention is not restricted to the exemplary embodiments. The exemplary embodiments are illustrated schematically in the Figures. Here, the same reference signs in the individual Figures denote identical or functionally identical elements, or elements which correspond in terms of their function.

FIGS. 2A to 2C show various perspective illustrations of an exemplary embodiment of a sampling system;

FIGS. 3A to 3D show a sampling cycle for clarifying an exemplary embodiment of a method for collecting a liquid sample performed using the sampling system as per FIGS. 2A to 2C;

FIG. 4 shows an alternative exemplary embodiment of a rotational-direction sensitive element;

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of the present invention.

Figure 1B:
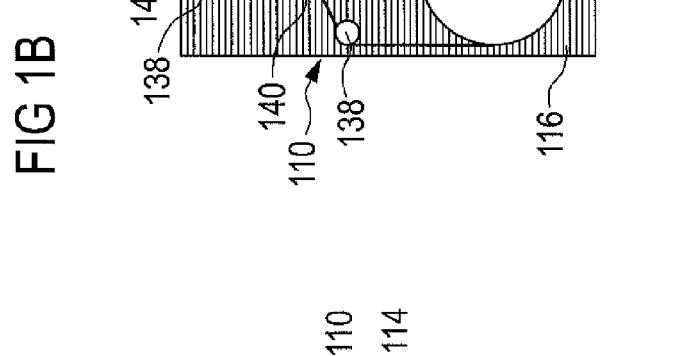
FIGS. 1A and 1B show a basic concept of a sampling system with an analysis tape.
Figure 1A:
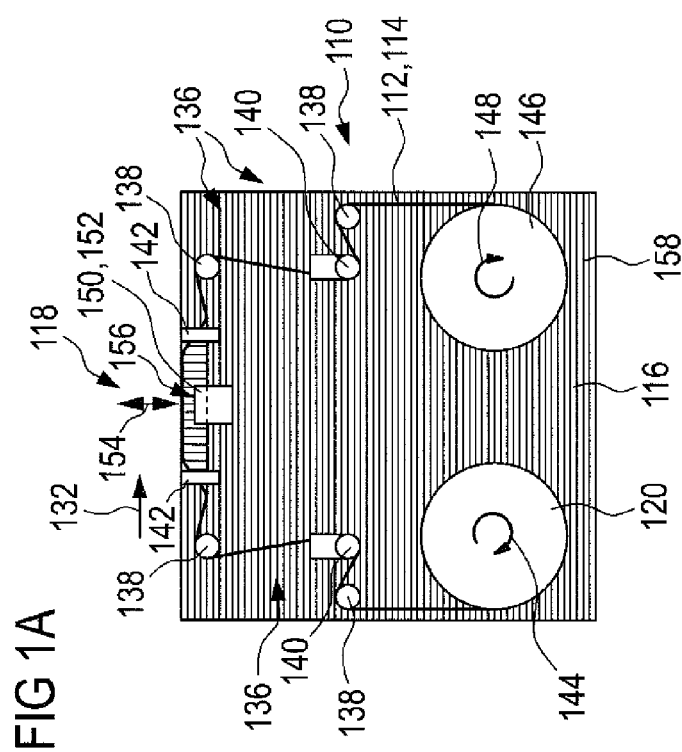
Figure 1C:
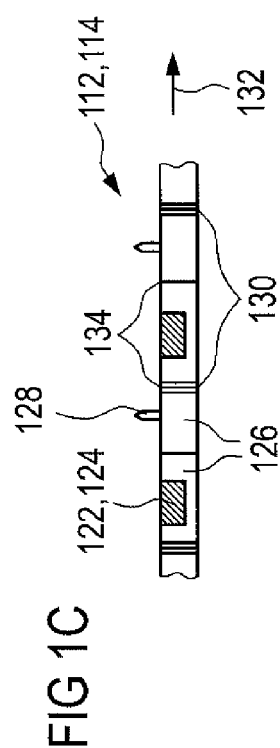
FIG. 1C shows an exemplary embodiment of an analysis tape.

FIGS. 1A and 1B schematically illustrate, in a plan view, a basic concept of an exemplary embodiment of a sampling system 110. In this case, the sampling system uses an analytic auxiliary means 112 in the form of an analysis tape. An exemplary embodiment of such an analysis tape 114 is illustrated in FIG. 1C in an exemplary fashion.

In these FIGS. 1A and 1B, and in the subsequent Figures, the sampling system is merely illustrated in an exemplary fashion and in cross section and can comprise further components which are not illustrated. In particular, it can comprise further electronic components, for example, components for performing and evaluating a qualitative and/or quantitative analysis of a sample (e.g., an electronic control, display elements, input and output means and/or further components). The parts of the sampling system 110 illustrated in the Figures are mounted on a base plate 116. In addition, further components can be present, in particular, a housing surrounding the base plate 116, for example, a housing which has an opening (e.g., an opening which can be closed off by a flap and/or a slider) in an application position 118 of the sampling system 110, by means of which opening the analytic auxiliary means 112 can be accessed.

FIGS. 1A and 1B merely illustrate a schematic guide of the analysis tape 114. Further details of a drive system are not illustrated; these are accentuated in more detail in the subsequent FIGS. 2A to 3D.

As shown in FIGS. 1A and 1B, the analysis tape 114 is firstly held on a supply reel 120 which is designed as a coil with the analysis tape 114 wound up thereon. By illustrating a section of this analysis tape 114, FIG. 1C clarifies that the analysis tape 114 comprises alternately arranged test elements 122 in the form of test fields 124. These test fields 124 can, for example, be printed on and/or laminated on and/or adhesively bonded to a carrier tape 126 and contain a test chemical which changes at least one chemical or physical property on contact with the at least one analyte to be detected. By way of example, this can be a property which can be detected by electrochemical means and/or a property which can be detected by optical means, e.g., a change in color.

Lancets 128 are respectively applied to the carrier tape 126 between the test elements 122. Herein, the test fields 124 and the lancets 128 are arranged on the carrier tape 126 such that these face toward the same side of this carrier tape 126. Each of these lancets 128 and test fields 124 or test elements 122 on its own forms a single analytic auxiliary means 112 and so both the entirety of the analytic auxiliary means and an individual analytic auxiliary means 112 can be referred to in the same way within the scope of the present invention. In the illustrated exemplary embodiment, in which lancets 128 and test fields 124 are used, respectively, one lancet 128 and one test element 122 form a pair 130 of analytic auxiliary means 112 assigned to one another, with the test field 124 respectively assigned to the lancet 128 being arranged behind said lancet 128 in a running direction 132 of the analysis tape 114. Markings 134 are printed onto the carrier tape 126 between the individual analytic auxiliary means 112, that is to say between the lancets 128 and the test fields 124. By way of example, these markings 134 can be detected optically by the sampling system 110 for thus positioning in the application position 118 a certain analytic auxiliary means 112 of the analysis tape 114.

However, other embodiments of the analytic auxiliary means 112, the analysis tape 114 and the lancets 128 and test elements 122 than those of the embodiment illustrated in FIG. 1C are also feasible. Thus, for example, there can also be an analysis tape 114 onto which only test fields 124 have been applied, without lancets 128 being present, or an analysis tape 114 which only comprises lancets 128.

In FIGS. 1A and 1B, the analysis tape 114 is guided from the supply reel 120 to the application position 118 via a roller system 136 which comprises fixed rollers 138 and moveable rollers 140. Here, the roller system 136 is designed such that the alignment of the analysis tape 114 is deflected by a deflection system 142, which comprises deflection rollers, just before it reaches the application position 118. Whereas, away from the application position 118, the roller system 136 basically guides the analysis tape 114 in a plane in which the analysis tape 114 is arranged perpendicularly to the plane of the drawing in FIGS. 1A and 1B (i.e., perpendicular to the base plate 116), in the application position 118 this analysis tape 114 is brought into an essentially parallel alignment with the base plate 116 by the deflection system 142. This parallel alignment ensures that a deflection of the analysis tape 114 in the application position 118 (see below, cf. FIGS. 1A and 1B) can move a side edge of the analysis tape 114 (the upper edge of the analysis tape 114 in FIG. 1C) toward sampling. By way of example, this can be used (as explained in more detail below) for taking up a liquid sample on the test field 124 which is arranged in the application position 118, or for performing a lancet movement by that lancet 128 which is arranged in the application position 118.

The movement direction of the analysis tape 114 in FIGS. 1A and 1B is indicated by the arrow 132. Thus, the individual analytic auxiliary means 112 are brought (cycled) into the application position 118 in succession, with the supply reel 120 being rotated in an unwinding direction 144 (clockwise in FIG. 1A). Used analytic auxiliary means 112, that is to say test fields 124 onto which a liquid sample was applied or lancets 128 which were used for a lancet movement, are subsequently moved via the roller system 136 to a take-up reel 146 which is rotated in a winding direction 148 (likewise clockwise in this exemplary embodiment). This, for example, ensures that these analytic auxiliary means 112 are not reused but are disposed of safely and hygienically and without risk to a user.

FIGS. 1A and 1B furthermore illustrate a coupling piece 150, which forms part of a coupling element 152 (not illustrated fully in FIGS. 1A and 1B, see the subsequent Figures) and which is moveably mounted in a deflection direction 154 (illustrated in FIG. 1A by a double-headed arrow). Here, the deflection direction 154 in the application position 118 is basically perpendicular to the movement direction 132 of the analysis tape 114. Here, FIG. 1A shows a non-deflected position of the coupling piece 150 and the analytic auxiliary means 112 in the application position 118, whereas FIG. 1B shows a deflected position of these elements. By way of example, the coupling piece 150 can comprise a slit 156 which is embedded in the coupling piece 150 and through which the analysis tape 114 is guided such that the application edge (that is to say the upper edge in FIGS. 1A and 1B) remains accessible, for example, for applying a liquid sample and/or for a lancet movement. The analysis tape 114 can be guided through this slit 156 in a gliding fashion.

In the process, the coupling piece 150 is attached to further parts of the coupling element 152 which, in the application position 118, make a deflection of the analysis tape 114 possible and which are driven by a drive unit (see the following Figures) in order to effect the deflection movement. The purpose of the moveable rollers 140 in this case is that of preventing the formation of tension within the analysis tape 114 during the deflection (see FIG. 1B) because these moveable rollers 140 are in an upper state in the deflected position (cf. FIG. 1B compared to FIG. 1A) and as a result of this the tension on the analysis tape 114 caused by the deflection is compensated for.

The entire part of the sampling system 110 shown in FIGS. 1A and 1B can, for example, be produced by the separate introduction of individual elements or a number of these elements into the sampling system 110. Thus, it would, for example, be feasible to separately introduce the supply reel 120 and the take-up reel 146 into the sampling system 110 and to correspondingly thread the analysis tape 114 through the roller system 136, like threading film into a camera. A used analysis tape 114 could in this fashion be replaced by an unused, new analysis tape 114.

However, since this threading would only be able to be performed with difficulty, particularly in the case of physically handicapped patients who are not uncommon among diabetics, it is typical for the part of the sampling system 110 illustrated in FIGS. 1A and 1B to be designed as a tape cassette 158. In this case, the tape cassette 158 may comprise at least the optional base plate 116, the supply reel 120, the take-up reel 146 and at least parts of the optional roller system 136. The coupling piece 150 can also accordingly be part of this tape cassette 158. The tape cassette 158 can furthermore comprise a housing (not illustrated in FIGS. 1A and 1B) which makes possible a coupling of further elements of the sampling system 110 onto the supply reel 120, the take-up reel 146 and possibly the coupling piece 150. This affords the possibility of completely introducing the tape cassette 158 into the sampling system 110 as a separate component and, for example, coupling said tape cassette onto a drive unit and/or further parts of the coupling element 152 there. This means that even physically handicapped patients can easily insert new analytic auxiliary means 112 into the sampling system 110 by replacing a complete tape cassette 158.

Figure 2A:
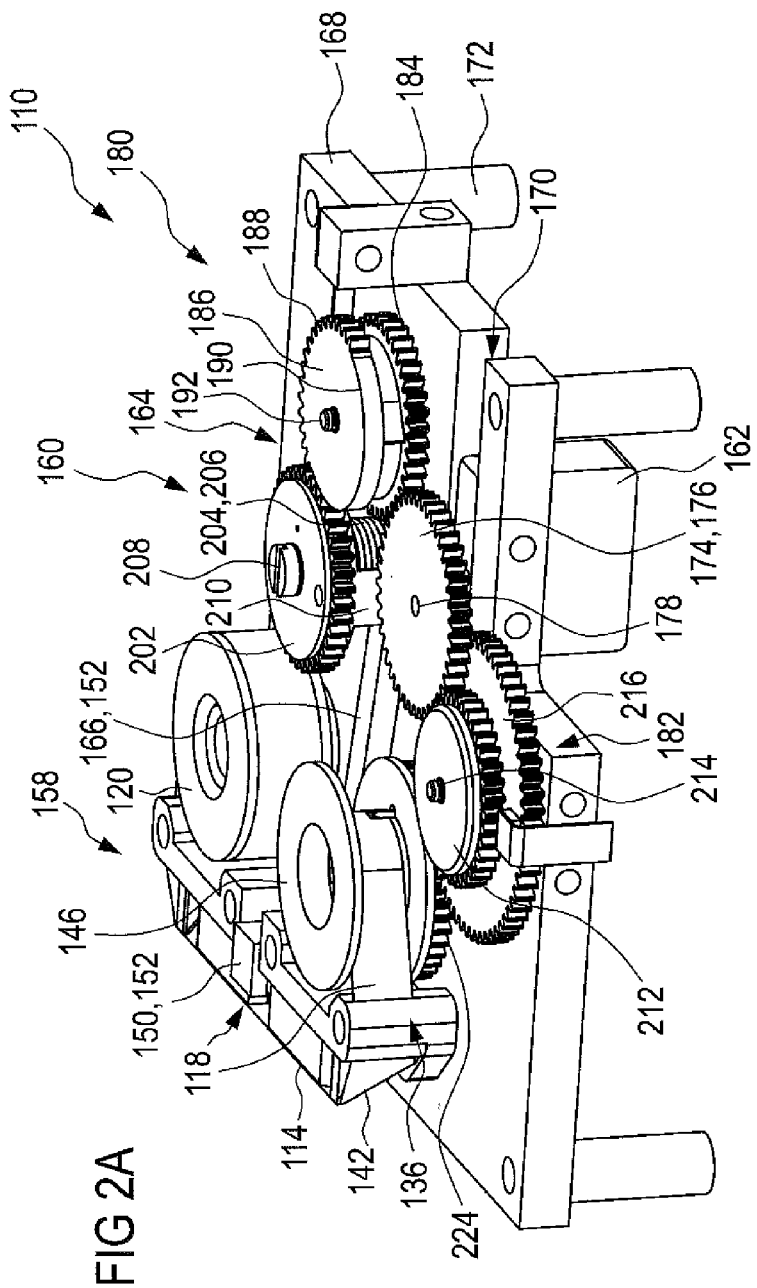
Figure 2C:
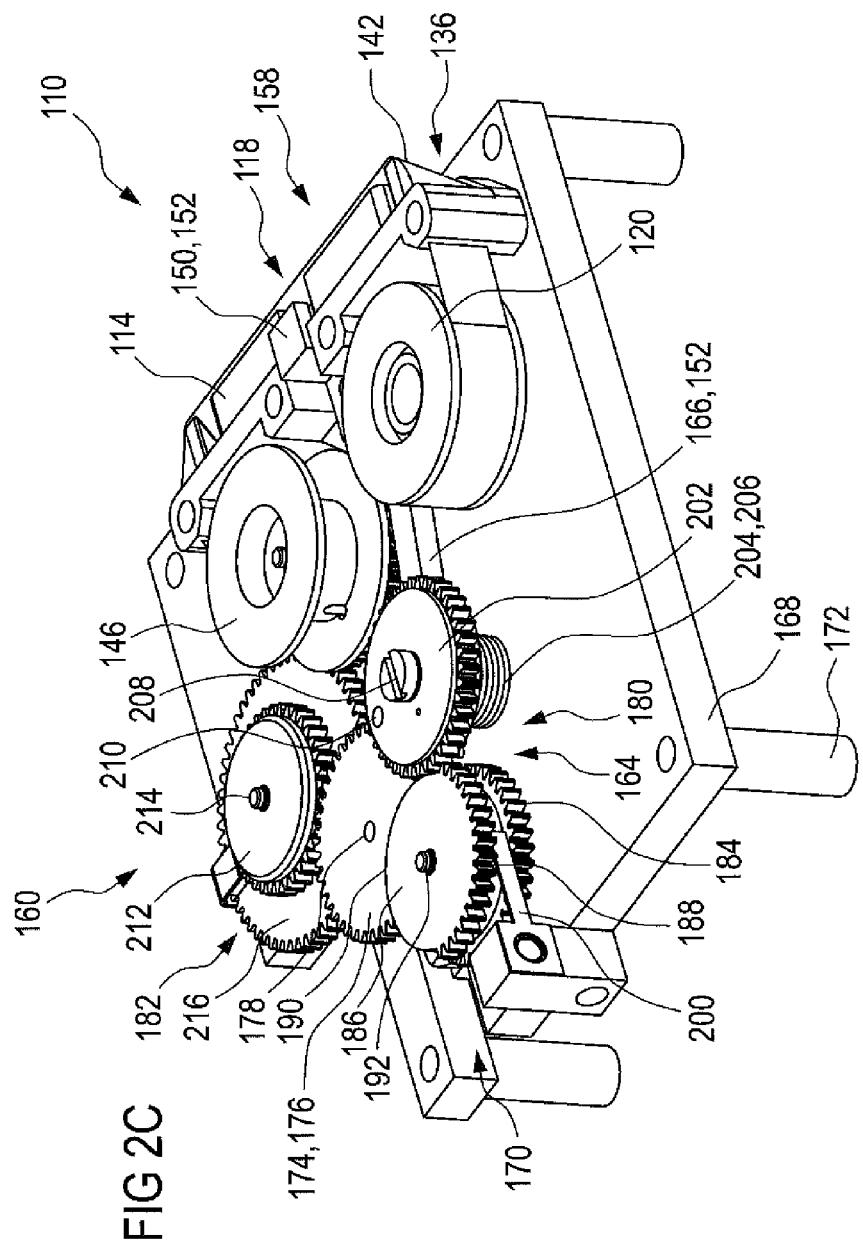

FIGS. 2A to 2C illustrate different perspective illustrations of an exemplary embodiment of a sampling system 110, the functioning of which system will subsequently be explained on the basis of a sequence illustrated in FIGS. 3A to 3D. The sampling system 110 is typically designed for operation with a tape cassette 158 for an analysis tape 114 which can, for example, be designed analogously to the example illustrated in FIGS. 1A and 1B. However, this tape cassette 158 is only illustrated in part in FIGS. 2A to 2C and so, for example, the base plate 116 is not shown since it would conceal additional essential elements of the tape cassette 158. In FIGS. 2A to 2C, this base plate would be located above the illustrated design.

The tape cassette 158 again comprises a supply reel 120, a take-up reel 146 and a roller system 136, a deflection system 142 and a coupling piece 150. Here, the roller system 136 is only illustrated rudimentarily in FIGS. 2A to 2C and has a design which deviates slightly from the roller system 136 illustrated in FIGS. 1A and 1B. However, analogously, it is also possible to use a roller system 136 as per FIGS. 1A and 1B, in particular a roller system 136 with fixed rollers 138 and moveable rollers 140 which prevent a build-up of tension within the analysis tape 114.

Likewise not illustrated in FIGS. 2A to 2C is a possible housing of the tape cassette 158, or, once again, further components of the sampling system 110 such as, for example, an electronic control, and input means, display elements, data stores, evaluation devices for qualitative and quantitative analysis of the liquid sample, a housing of the sampling system 110 or similar elements.

The sampling system 110 in FIGS. 2A to 2C furthermore comprises a drive unit 160 for driving the functions of the sampling system 110. The drive unit 160 in turn comprises an energy transducer which, without restricting possible designs of the energy transducer, is in this case designed as an electromechanical energy transducer in the form of a motor 162. The motor 162 is designed as an electric motor. The drive unit 160 furthermore comprises a toothed transmission 164 which couples onto a coupling element 152. In addition to the coupling piece 150, already mentioned in FIGS. 1A and 1B and forming part of the tape cassette 158, this coupling element 152 comprises, as an additional element, a connecting rod 166 as a connecting element in the exemplary embodiment illustrated in FIGS. 2A to 2C, said connecting rod 166 coupling onto the coupling piece 150 and being able to effect the deflection movement along the deflection direction 154 in FIGS. 1A and 1B.

In the exemplary embodiment illustrated in FIGS. 2A to 2C, the entire drive unit 160 is attached to a base plate 168. Here, the motor 162 is fixed in a motor guide 170 in the form of a slit in the base plate 168 such that a large part of this motor 162 is arranged below the base plate 168 (that is to say on the opposite side of the base plate 168 from the gearwheel transmission 164). Moreover, the base plate 168 has supports 172 by means of which the base plate 168 can, for example, be assembled in a housing of the sampling system 110. However, in addition to this embodiment of the assembly of the drive unit 160 illustrated in an exemplary fashion in FIGS. 2A to 2C, many additional options are feasible for designing or fixing this drive unit and so the example is merely intended for illustrative purposes.

The gearwheel transmission 164 comprises a multiplicity of gearwheels coupled to one another in various ways. The starting point is a motor gearwheel 174 which acts as the first drive wheel and is connected to a motor axle 178 of the motor 162 in a rotationally secured fashion. This motor gearwheel 174 is connected to a first drivetrain 180 and a second drivetrain 182, which drivetrains drive different system functions.

The first drivetrain 180 comprises a piercing drive gearwheel 184 which engages directly in the motor gearwheel 174 and thus counter-rotates with respect to this motor gearwheel 174. Above this piercing drive gearwheel 184, the first drivetrain 180 furthermore comprises a release gearwheel 186 (only illustrated in FIGS. 2A and 2C, omitted in FIG. 2B), which is only toothed over nearly half of its circumference and thus has a first, toothed circumferential region 188 and a second, untoothed circumferential region 190. Although the release gearwheel 186 is mounted on a common axle 192 with the piercing drive gearwheel, it is not connected to this axle 192 in a rotationally secured fashion but is merely mounted in a sliding fashion thereon. Furthermore, the release gearwheel 186 and the piercing drive gearwheel 184 are connected by a first rotational-direction sensitive element 194 arranged between these elements in the form of a first freewheel 196. This first freewheel 196 can be seen in the illustration as per FIG. 2B, in which the release gearwheel 186 was omitted, and it is likewise mounted on the axle 192 and fixed to the piercing drive gearwheel 184 in a rotationally secured fashion. The freewheel 196 comprises freewheel arms which, starting from the axle 192, extend spirally in a counterclockwise fashion around this axle. These freewheel arms 198 or the ends of these freewheel arms 198 engage in driving pins or differently designed driver elements (not visible in FIGS. 2A to 2C) on the underside of the release gearwheel 186. This means that if the piercing drive gearwheel 184 in FIGS. 2A to 2C rotates counterclockwise, this piercing drive gearwheel 184 drives the release gearwheel 186, whereas these two gearwheels 184, 186 are decoupled from one another in the opposite rotational direction. In other words, the motor gearwheel 174 only additionally drives the release gearwheel 186 in the case of clockwise movement, whereas the release gearwheel 186 is decoupled from the motor gearwheel 174 in an opposite rotational direction and does not co-rotate.

This embodiment of the first rotational-direction sensitive element 194 illustrated in FIG. 2B merely constitutes an option for embodying such rotational-direction sensitive elements which effect driving in one direction but decoupling in another rotational direction. Thus, by way of example, it would also be possible for different types of freewheels to be used, for example, freewheels with a greater number of freewheel arms 198 or a different embodiment of these freewheel arms. Freewheels with such freewheel arms 198, which can, for example, be designed as arms or prongs or catches, are generally referred to as catch freewheel arms within the scope of the present invention. Since an excessive spread of the freewheel arms 198 would lead to strong noise generation during the operation of the sampling system 110 and to an increased dead travel of the first freewheel 196, it is advantageous for a freewheel lock to be provided which reduces the dead travel and reduces the noise generation. Such an optional freewheel lock is not provided in the illustrated embodiment of the first freewheel 196, but it could be additionally implemented.

Furthermore, the first drivetrain 180 comprises a piercing spring gearwheel 202 which engages with the release gearwheel 186 (at least in a few angular positions). This piercing spring gearwheel 202 is connected in a rotationally secured fashion to a mechanical energy store 204 in the form of a spiral piercing spring 206. Here, one end of this piercing spring 206 is connected to the piercing spring gearwheel 202, whereas another end of this piercing spring 206 has a fixed location. In the process, the piercing spring 206 is arranged about an axle 208 of the piercing spring gearwheel 202 such that a clockwise rotation of the piercing spring gearwheel 202 effects a tensioning of the piercing spring 206 and hence a charging of the mechanical energy store 204, whereas a counterclockwise rotation of the piercing spring gearwheel 202 effects a relaxation of the piercing spring 206 and hence a discharging of the mechanical energy store 204.

Figure 2E:
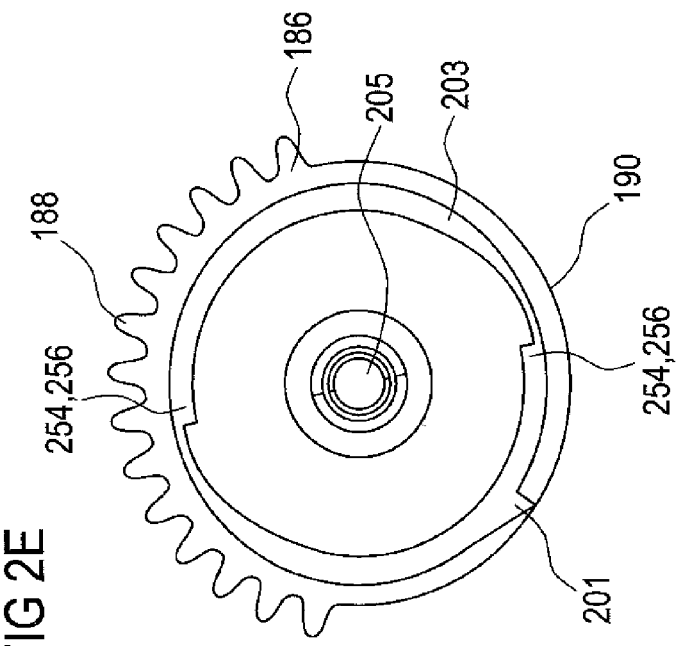
FIG. 2E shows a view of a release gearwheel.
Figure 2D:
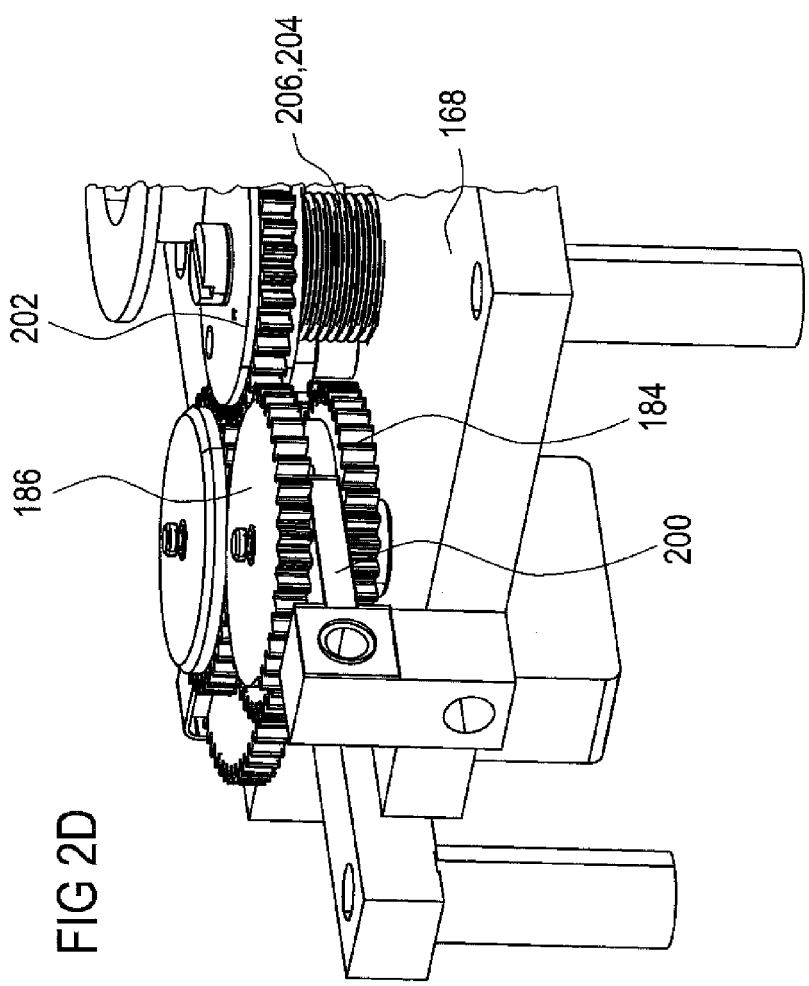
FIG. 2D shows a partial perspective view of a drivetrain.

Furthermore, a lock 200 is provided on the release gearwheel 186, which lock is fixedly connected to the base plate 168 and the function of which is intended to be explained on the basis of FIGS. 2D and 2E. Here, FIG. 2D shows a partial perspective view of the first drivetrain 180 which clarifies that the lock 200 engages into the release gearwheel 186. In a tensioned state of the piercing spring 206, the lock 200 is used to prevent an abrupt relaxation of this piercing spring 206 as a result of a rotation of the piercing spring gearwheel 202 (counterclockwise rotation) and the release gearwheel 186 (clockwise rotation). By way of example, the lock 200 has an elastic design (e.g., as a leaf spring) and engages with a catch 201 protruding from the circumferential side on the underside of the release gearwheel 186. This catch 201 can be seen in FIG. 2E, which shows a view of the release gearwheel 186 from below. The catch 201 is arranged on the outer side of a catch ring 203 which is arranged on the underside of the release gearwheel 186, that is to say on the side of this release gearwheel 186 facing the freewheel arms 198. On its inner side, the catch ring 203 has a toothed structure 254 with two teeth 256 which interact with the two freewheel arms 198 and form the first rotational-direction sensitive element 194 with the latter. Furthermore, in this illustration, the release gearwheel 186 has a bore 205 for holding the axle 192. The catch 201 is positioned on the circumferential side such that it is held by the lock 200 (e.g., in an interlocking fashion) in the tensioned position of the piercing spring 206 and so the release gearwheel 186 can only be rotated counterclockwise. The release mechanism will be explained in more detail below on the basis of FIGS. 3A to 3D.

The piercing spring gearwheel 202 is connected to the connecting rod 166 of the coupling element 152 via an eccentric bolt 210 and so a rotational movement of the piercing spring gearwheel 202 can be directly converted into a movement of the connecting rod 166 and thus, via the coupling piece 150, into a deflection of the analytic auxiliary means 112 located in the application position 118. As described above, these deflections can in this case take different forms for the various analytic auxiliary means 112 and so, for example, there can be a different deflection for a lancet 128 (i.e., for example, a different deflection distance) than for a test element 122. This can be performed in a number of ways, for example, by virtue of the fact that use is made of a crank drive with different cranks for the lancet 128 and the test element 122. By way of example, the position of the lancet 128 relative to the analysis tape 114 also influences the puncture depth. Various other embodiment variants are feasible.

Thus, the first drivetrain 180 is basically used for the deflection of the analytic auxiliary means 112, for example, for a piercing movement of a lancet 128 and/or a sampling movement of a test element 122. By means of the first drivetrain 180, these various system functions are coupled onto the motor gearwheel 174 and hence onto the motor 162. As described above, this coupling is merely carried out in the case where the motor gearwheel 174 rotates clockwise.

Furthermore, the sampling system 110 as per FIGS. 2A to 2C also comprises the second drivetrain 182. This drivetrain 182 first of all comprises a reel drive gearwheel 212 which engages with the motor gearwheel 174. By way of example, if the motor gearwheel 174 rotates clockwise, the reel drive gearwheel 212 rotates counterclockwise.

Together with the reel drive gearwheel 212, a transport gearwheel 216 is held on an axle 214 of the reel drive gearwheel 212, but said transport gearwheel is not connected to the reel drive gearwheel 212 in a rotationally secured fashion. Furthermore, the reel drive gearwheel 212 and the transport gearwheel 216 are connected to each other via a second rotational-direction sensitive element 218 which in turn can be designed as a second freewheel 220 in this exemplary embodiment. For the embodiment of this second freewheel 220, reference can be made to the above description of the first freewheel 196 and so both freewheels 196, 220 can, for example, have an identical design. Again, a freewheel lock can also be provided for reducing the dead travel and for suppressing the development of noise, said lock is merely indicated in FIG. 2B and denoted by the reference sign 222.

Here, the second freewheel 220 is designed such that it only drives the transport gearwheel 216 when the reel drive gearwheel 212 rotates clockwise. By contrast, if the reel drive gearwheel 212 rotates counterclockwise, there is no coupling between this reel drive gearwheel 212 and the transport gearwheel 216. Or, expressed in the rotational sense of the motor gearwheel 174, there merely is a coupling of this motor gearwheel 174 to the transport gearwheel 216 when the motor gearwheel 174 rotates counterclockwise. Thus, the second drivetrain 182 is only coupled to the drive by the motor 162 when the motor gearwheel 174 rotates counterclockwise; by contrast, if the motor 162 rotates clockwise, said second drivetrain is decoupled from the motor.

The transport gearwheel 216 in turn engages with a reel gearwheel 224, as is shown in FIG. 2B, for example. This reel gearwheel 224 is connected in a rotationally secured fashion to the take-up reel 146 (for example, by means of a toothing) and drives the latter. Since, in the illustrated embodiment of the drive unit 160, the transport gearwheel 216 can only be driven by the motor 162 in a clockwise direction, the take-up reel 146 can only be driven counterclockwise, that is to say a rotational movement of this take-up reel 146 in which the analysis tape 114 is wound onto this take-up reel 146. Reference is made here to the fact that, as an example, it is only the take-up reel 146 that is driven in the sampling system 110 illustrated in an exemplary fashion in FIGS. 2A to 2C. However, alternatively, a different embodiment of the drive would be feasible, for example, an embodiment in which merely the supply reel 120 would be driven (with the winding onto the take-up reel 146, for example, possibly being effected by a spring drive of this take-up reel 146), or an embodiment in which there was a combined drive, in which both the supply reel 120 and the take-up reel 146 are driven.

The functioning of the sampling system 110 illustrated in FIGS. 2A to 2C and a method of collecting a liquid sample are intended to be illustrated step-by-step in the following text on the basis of FIGS. 3A to 3D. These FIGS. 3A to 3D show a plan view of the sampling system 110 illustrated in FIGS. 2A to 2C and so reference can extensively be made to these Figures and the description of these Figures for the functioning and embodiment of the individual elements.

Figure 3A:
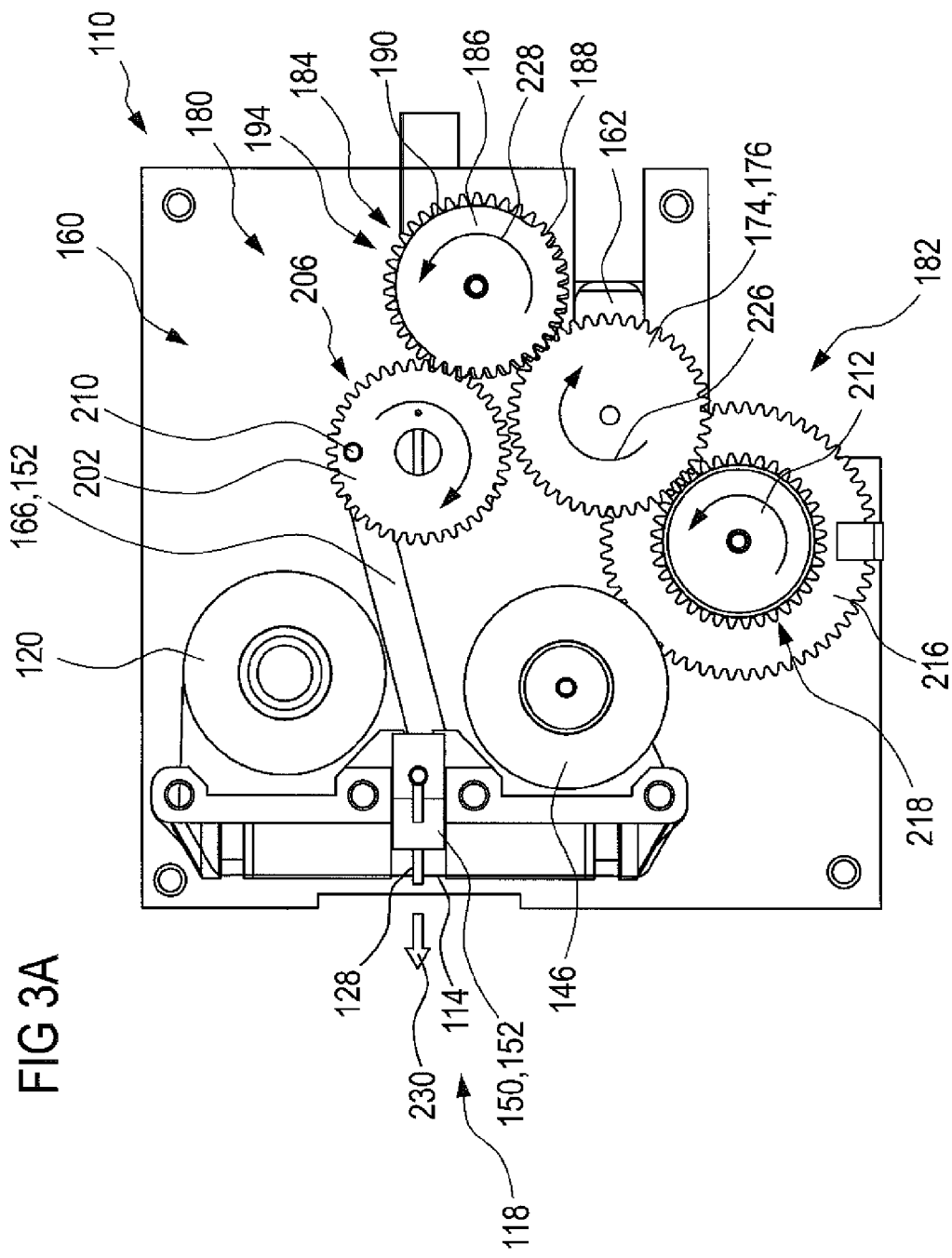

In this case, the starting point is the situation of the sampling system 110 illustrated in FIG. 3A. However, since the proposed method is typically a cyclical method, in which the individual method steps (operational phases) are respectively carried out repeatedly one after the other, it would just as easily be possible to start the method at a different point, for example, with FIG. 3B.

The starting point is the situation illustrated in FIG. 3A, in which a lancet 128 is located in the application position 118. The connecting rod 166 is arranged such that it is located in an upper position in which the eccentric bolt 210 is approximately arranged in a 12 o'clock position of the piercing spring gearwheel 202. The piercing spring 206 is tensioned in this position of the piercing spring gearwheel 202, that is to say the mechanical energy store 204 is charged (this is not visible in FIG. 3A because it is concealed by the piercing spring gearwheel 202). The release gearwheel 186 is in a position in which the toothed circumferential region 188 still just engages into the teeth of the piercing spring gearwheel 202. Since, as described above, the lock 200 in turn holds the release gearwheel 186 and the clockwise rotation thereof is prevented, the piercing spring gearwheel 202 is still just held in the tensioned position in this fashion.

The actual release procedure follows thereafter, starting from the position illustrated in FIG. 3A. For this purpose, the motor gearwheel 174 is rotated clockwise, as indicated in FIG. 3A by the arrow 226. This rotation 226 is converted to a counterclockwise rotation 228 of the piercing drive gearwheel 184 and, from there, to the release gearwheel 186 via the first rotational-direction sensitive element 194. However, this rotation 228 causes the toothed circumferential region 188 of the release gearwheel 186 to disengage from the teeth of the piercing spring gearwheel 202 and so the piercing spring gearwheel 202 is released. This piercing spring gearwheel 202 is now no longer held in the tensioned position illustrated in FIG. 3A, but relaxes by a counterclockwise rotation. In the process, the drive unit 160 drives the connecting rod 166 via the piercing spring gearwheel 202, which connecting rod in turn is coupled to the lancet 128 in the application position 118 via the coupling piece 150 and drives said lancet into a deflected position. In other words, the lancet 128 is driven to a piercing movement via the coupling element 152, which movement is denoted in FIG. 3A by the reference sign 230. When the eccentric bolt 210 has reached its 9 o'clock position the lancet 128 reaches its maximum deflection. Subsequently the connecting rod 166 once again returns since the piercing spring 206 continues to relax. The analysis tape 114 also returns into its non-deflected position. This return movement can, for example, be effected actively by the coupling element 152 and/or can be driven in another fashion, for example, by inherent tension in the analysis tape 114. This clarifies that this exemplary embodiment comprises a passive coupling of the coupling element 152 to the analytic auxiliary means 112. There is in each case a separate coupling onto each individual analytic auxiliary means 112 in the application position 118, and only a forward movement is driven. However, alternatively, an active coupling would also be possible, in which the return movement of the lancet 128 or the analytic auxiliary means 112 would also be driven. This piercing movement 230 of the lancet 128, for example, effects a perforation of an area of skin of a patient, as a result of which, for example, a drop of blood is generated.

In this release process with a clockwise rotation 226 of the motor gearwheel 174, it is still only the reel drive gearwheel 212 that is driven by the motor gearwheel 174 but not, by contrast, the transport gearwheel 216. This can be attributed to the rotational-direction sensitivity of the second rotational-direction sensitive element 218. Thus, the take-up reel 146 is not moved during this process and the reel drive gearwheel 212 co-rotates idly and without actuating the remainder of the second drivetrain 182.

FIG. 3B illustrates a second operational phase of the sampling system 110, which, for example, follows the operational phase in FIG. 3A. Whereas, in the phase as per FIG. 3A, the first drivetrain 180 was coupled to the motor gearwheel 174 in order to initiate the piercing movement 230 system function, the second drivetrain 182 is now coupled to the motor gearwheel 174 in the process illustrated in FIG. 3B in order to effect an onward transport of the analysis tape 114. During this sequence, the piercing spring 206 is in a relaxed position in which the eccentric bolt 210 is in a 6 o'clock position. This relaxed position can be designed in a defined fashion, for example, by the provision of a defined stop and/or by the piercing spring 206 being loaded with a mechanical pretension.

The rotational direction of the motor 162 is reversed during this second operational phase, and can, for example, be carried out via a control by reversing the polarity of this motor 162. The motor gearwheel 174 accordingly performs a counterclockwise rotational movement 232. The reel drive gearwheel 212 accordingly rotates in a clockwise direction, which in FIG. 3B is denoted by the reference sign 234. As a result of the rotational-direction sensitivity of the second rotational-direction sensitive element 218, the reel drive gearwheel 212 drives the transport gearwheel 216 and so the latter also performs a clockwise rotation 234. As described above, the transport gearwheel 216 engages into the reel gearwheel 224 and so the take-up reel 146 performs a rotation 236 in the counterclockwise direction. As a result of this, the analysis tape 114 is wound onto the take-up reel 146. A corresponding control of the duration of the rotation or of the rotational angle of the motor gearwheel 174 (which, for example, can in turn be performed by a control of the sampling system 110) can bring about the driving of precisely one test element 122 in the form of a test field 124 into the application position 118. This typically is the test element 122 on the analysis tape 114 following the lancet 128 used in FIG. 3A. By way of example this affords the possibility of advancing by precisely one analytic auxiliary means 112 on the analysis tape 114.

As a result of the reversed rotational-direction sensitivity of the first rotational-direction sensitive element 194, the first drivetrain 180 is decoupled from the motor gearwheel 174 during this sequence and so the piercing spring gearwheel 202 and the release gearwheel 186, for example, do not co-rotate. Although the piercing drive gearwheel 184 (concealed in FIG. 3B) co-rotates, it is decoupled from the release gearwheel 186 by means of the first rotational-direction sensitive element 194. This ensures that the connecting rod 166 does not change during this partial sequence. Thus, the result of the partial sequence illustrated in FIG. 3B is that once again a new analytic auxiliary means 112 in the form of a test element 122 with a test field 124 is located in the application position 118. Here, the piercing spring 206 is relaxed, i.e., the energy store 204 is discharged. That is to say the counterclockwise rotation of the motor gearwheel 174 is used in the partial sequence illustrated in FIG. 3B in order to couple onto the motor 162 via the second drivetrain 182 the system function of advancing the analysis tape 114.

FIG. 3C shows a third partial sequence, in which the first drivetrain 180 is again coupled to the motor 162. Here, the motor 162 is driven in this partial sequence such that it once again performs a clockwise rotation 226, as in FIG. 3A. As a result of the rotational-direction sensitivity of the second rotational-direction sensitive element 218, the reel drive gearwheel 212 does co-rotate in the counterclockwise direction, but the transport gearwheel 216 is decoupled therefrom by the second rotational-direction sensitive element 218 and is motionless. The analysis tape 114 therefore remains in the position in which the test element 122 is in the application position 118.

By contrast, the first drivetrain 180 is coupled because the motor gearwheel 174 drives the piercing drive gearwheel 184 to a rotation 228 and the latter in turn drives the release gearwheel 186 via the first rotational-direction sensitive element 194. This driving is carried out until the toothed circumferential region 188 of this release gearwheel 186 again engages into the teeth of the piercing spring gearwheel 202 and drives the latter to a clockwise rotation 238. Here, a number of processes occur simultaneously. On the one hand, the piercing spring 206 is tensioned again and so the mechanical energy store 204 is being charged. However, the eccentric bolt 210 moves the connecting rod 166 at the same time. In the process, the coupling piece 150 of the coupling element 152 reengages with the analysis tape 114 and deflects the test element 122 in the application position 118. When the eccentric bolt 210 is in the 9 o'clock position, the test element 122 is in the deflected position. Subsequently, as the eccentric bolt 210 moves from the 9 o'clock position toward the 12 o'clock position, there is a return movement of the test element 122 into the non-deflected position. This movement of the test element 122 can be used for taking up the sample. Thus, for example, the test field 124 can perform a sampling movement 240 in which the test field 124 is moved toward a previously perforated area of skin; there, for example, it takes up a drop of blood or another type of liquid sample and is subsequently returned.

Thus, this sampling movement is carried out in a gearwheel-driven fashion by the motor 174. Therefore, this sampling movement 240 is significantly slower than the preceding deflection of the analysis tape 114 during the piercing movement 230 and this is advantageous for the sampling. This can ensure that a sufficient amount of the liquid sample is applied to the test field 124.

As a result of the partial sequence of the sampling cycle illustrated in FIG. 3C, the piercing spring 206 is therefore again in the tensioned position, as in FIG. 3A, and a liquid sample was applied to the test field 124 in the application position 118. This partial sequence can be followed by a partial sequence (not illustrated), in which the sample is evaluated qualitatively and/or quantitatively. By way of example, the test field 124 can for this purpose be illuminated by light in the application position 118 and suitable detectors can determine, for example, color changes in test chemicals in the test field 124, from which in turn an analyte concentration (for example, a blood glucose concentration) in the liquid sample can be deduced. Alternatively or additionally, an electrochemical evaluation is also possible, for example, by electrically contacting the analysis tape 114 or the test field 124. However, in general, the measurement of the analyte concentration can advantageously be performed in a different position to the application position 118, both in the illustrated example and in other exemplary embodiments. Thus, for example, provision could be made of at least one separate measurement position into which the test field 124 is moved (for example, within the scope of a subsequent method step) and in which this test field 124 is evaluated, for example, by optical and/or electrochemical means. This transport of the test field 124 into the measurement position could, for example, be carried out simultaneously with the transport step described in the following text on the basis of FIG. 3D or it could be implemented within the scope of a separate transport step.

Subsequently, there is once again a transport sequence in FIG. 3D, in which the analysis tape 114 is advanced by one position, that is to say by one analytic auxiliary means 112 and so there is once again a new lancet 128 in the application position 118. In this transport partial sequence as per FIG. 3D, the motor 162 is again driven such that the motor gearwheel 174 carries out a counterclockwise rotation 232, wherein the first drivetrain 180 is decoupled from the motor 162 by the first rotational-direction sensitive element 194.

However, analogously to FIG. 3B, the reel drive gearwheel 212 is once again driven by said first rotational-direction sensitive element and the second rotational-direction sensitive element 218 the transport gearwheel 216 and, by this in turn, the reel gearwheel 224 and so the take-up reel 146 again performs the counterclockwise rotational movement 236, as a result of which the analysis tape 114 is wound up. In this fashion, an appropriate advance (that is to say again by a corresponding control of the time period and/or of the rotational angle of the motor 162) can cause the lancet 128 following the test field 124 used in FIG. 3C to be advanced into the application position 118. Reference can accordingly be made to the description of FIG. 3B for the individual steps of this partial sequence as per FIG. 3D. The only difference to FIG. 3B that should be noted in this case is that, in this transport partial sequence as per FIG. 3D, the piercing spring 206 is tensioned and the eccentric bolt 210 is at the 12 o'clock position.

Thus, the result of the transport partial sequence as per FIG. 3D is again the starting point of the partial sequence in FIG. 3A. The cycle of partial sequences can accordingly start afresh, for example, to perform a new analysis.

As illustrated above, the use of the freewheels 196, 200 is merely one option for implementing rotational-direction sensitive elements 194, 218. However, alternatively or additionally, there are a number of additional options for implementing a coupling of the motor 162 and the motor gearwheel 174 to different drivetrains 180, 182 in different rotational directions such that in each case only one drivetrain is coupled or active. A further option for implementing a rotational-direction sensitive element 242 is illustrated in an exemplary fashion in FIG. 4. Here, a motor 162 which drives a motor axle 192 is once again used in this case. Again, there is a first drive wheel 176 in the form of a motor gearwheel 174 on this axle 192. However, said motor gearwheel is in this case connected to the axle 192 via a bolt 243 such that this motor gearwheel 174 can move in two planes 244, 246. On a first drive plane 244 (arranged at the top in FIG. 4), the motor gearwheel 174 is engaged with a drive element 248 of a first drivetrain, whereas on the second drive plane 246 (at the bottom in FIG. 4), the motor gearwheel 174 is engaged with a drive element

250 of a second drivetrain. Here, the two drivetrains do not necessarily have to be identical to the drivetrains 180, 182 in the exemplary embodiment as per FIGS. 3A to 3D, but can, for example, also be interchanged in relation to these.

The motor gearwheel 174 is arranged on the two planes 244, 246 by a circumferentially arranged groove 252 in the axle 192. The bolt 243 is held in this groove 252. This, for example, causes a counterclockwise rotation of the axle 192 (observed in FIG. 4 from above onto the axle 192) to "screw down" the motor gearwheel 174 onto the second drive plane 146, whereas a clockwise rotation of the axle 192 causes the motor gearwheel 174 to be arranged on the first drive plane 244 and hence be engaged with the drive element 248 of the first drivetrain. The groove 252 is designed in accordance with a helical curve. The drive elements 248, 250 of the two drivetrains can, for example, again be embodied as gearwheels. However, other embodiments are also feasible.

FIGS. 5A to 9 show a plurality of further exemplary embodiments of rotational-direction sensitive elements 194, 218 in the form of freewheels 196, 220 in different illustrations. What is illustrated in particular are embodiments of catch freewheels and a type of finger freewheel. However, as described above, this does not preclude the use of other types of freewheels.

If one of the illustrated freewheels 196, 220 is rotated more rapidly on a drive side in a work direction than on an output side, a driver in the form of freewheel arms 198 engages after a system-specific rotational angle (the dead travel) and transfers a maximum torque onto the output side. If the maximum torque is exceeded, the freewheel 196, 220 is destroyed. If the drive side rotates counter to the work direction, only a minimum torque, the idle torque, is transferred to the output side.

The freewheels 196, 220 suitable for the present sampling system 110 could, for example, transfer torques up to approximately 100 mNm and could have an idle torque which is approximately 0 mNm. Moreover, the freewheels 196, 220 should have a small installation size, a simple design, a robust construction and a short dead travel, and should operate quietly.

Figure 5B:
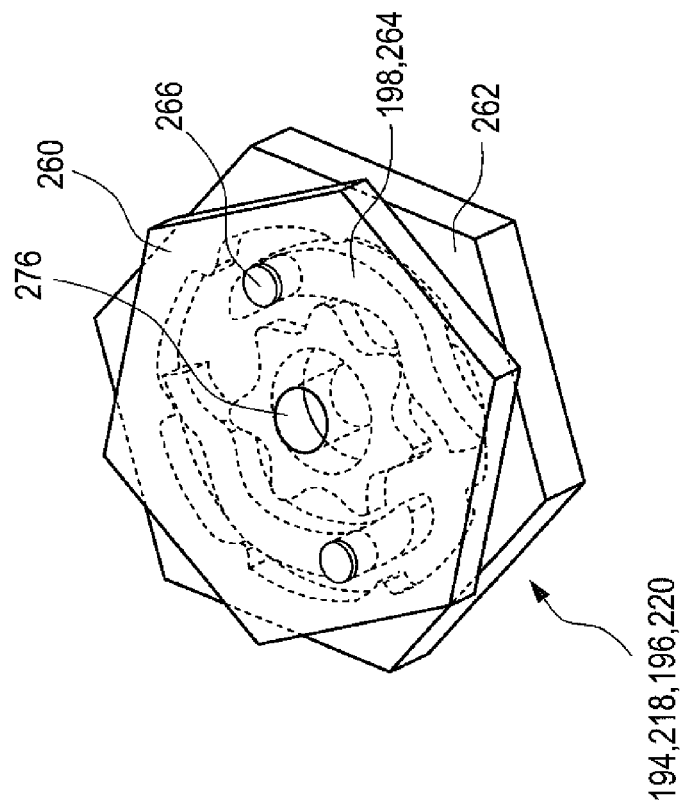
FIGS. 5A to 9 show a plurality of exemplary embodiments of freewheels which can be used as rotational-direction sensitive elements.
Figure 5A:
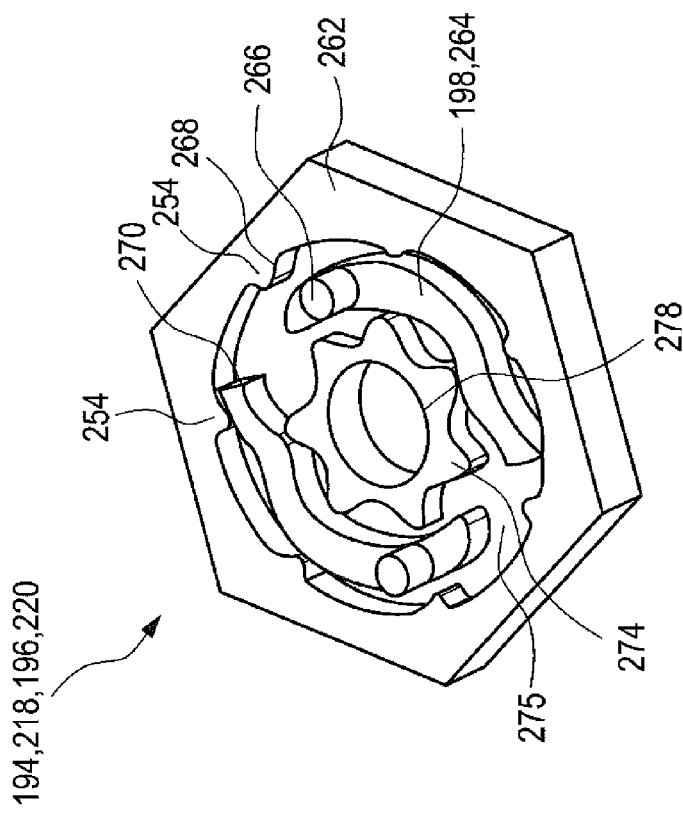

FIGS. 5A and 5B show various perspective illustrations of a first freewheel 196, 220 which is based on a freewheel in an automatic clock. This freewheel is designed for torques above 100 mNm and has a vanishingly small idle torque (<1 mNm).

This freewheel 196, 220 illustrated in FIGS. 5A and 5B is an exemplary embodiment of a so-called finger freewheel, that is to say a freewheel in which a drive side 260 or an output side 262 (in this case the drive side 260) is connected by at least one freewheel arm 198 in the form of a finger 264 which is mounted in a pivotable fashion about an axle 266. Two fingers 264 are provided in the illustrated exemplary embodiment. FIG. 5A shows the freewheel 196, 220 with a drive side 260 removed, whereas FIG. 5B illustrates the drive side 260 in a semitransparent fashion. Here, in this exemplary embodiment, drive side 260 and output side 262 are each designed as hexagonal disks; however, other embodiments are also feasible, for example, embodiments in the form of toothed disks.

The finger 264 is formed asymmetrically and interacts with a toothed structure 254 of the output side 262. In the case of a counterclockwise rotational movement of the drive side 260, the fingers 264 glide over flat flanks 268 of this toothed structure 254 without driving the output side 262. By contrast, in the case of a clockwise rotation, the driver ends 270 of the fingers 264 are pushed against steep flanks 272 of the toothed structure 254 and drive the output side 262. A second toothed structure 274 in the interior of the output side 262 ensures that the curved fingers 264 always lie against the outer toothed structure 254 in an optimal fashion. The toothed structure 254 and the second toothed structure 274 together form a channel 275 in which the fingers 264 run. Bores 276, 278 are respectively provided in the center of the drive side 260 and the output side 262, and one or more axles (not illustrated) are guided through these bores and can be connected to the drive side 260 and/or the output side 262. It is also possible for a different number of freewheel arms 198 to be provided instead of two freewheel arms 198, for example, an increased number which can, for example, be used to further reduce a dead travel.

Compared to other types of freewheels, the finger construction as per FIGS. 5A and 5B has a few advantages which are advantageous for medical applications in particular. The extremely low idle torque was already mentioned. For this, it is particularly advantageous if the freewheel 198, 264 is not acted upon by a lubricant, since such lubricants also cause a torque in the idle direction due to their viscosity. Instead, use can be made of free-moving materials, in particular plastics such as, for example, polyamide and/or polyacetal (POM). Alternatively, or additionally, use can also be made of metal parts. In this process, metal parts which are produced by a laser sintering process are particularly suitable.

A further reason for the idle torque being very low in the finger construction consists of the fact that, in the case of these freewheels, no elastic and/or plastic deformations of the freewheel arms 198 are necessary in the idle direction. Instead, the fingers 264 are of a rigid design and so forces which would have been required for a deformation can be dispensed with. At the same time, this construction of the freewheel arms 198 has a very robust design which leads to the high maximum torques of, in this example, over 100 mNm.

A further advantage of the design illustrated in FIGS. 5A and 5B lies in the extremely low noise development. Since, like in conventional elastic freewheel arms 198, there is no elastic deformation in this case which was undone in an abrupt fashion, no hard pieces abut against each other, which abutting could lead to the development of noise. Rather, the fingers 264 glide over the toothed structures 254, 278 and this only causes little noise.

Figure 6:
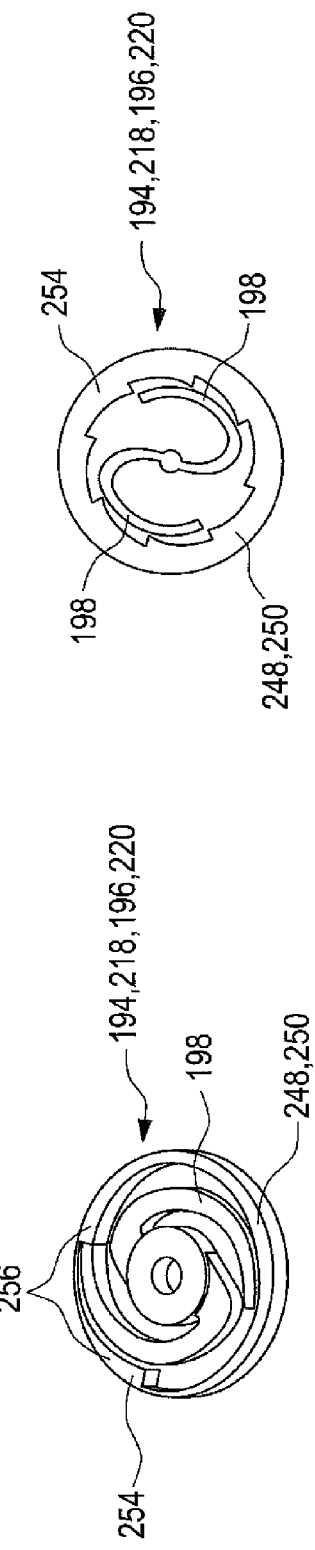

FIG. 6 illustrates an embodiment of a freewheel 196, 220 which basically corresponds to the freewheel 196 in FIG. 2B. The freewheel 196, 220 has two freewheel arms 198, which, in a work direction (a clockwise rotation of the arms in FIG. 6), engage in a toothed structure 254 of a drive element 248, 250 to be driven. However, there is no driving in the opposite direction since the freewheel arms 198 glide over the toothed structure 254. In the example as per FIG. 6, the toothed structure 254 in this case has two teeth 256. The freewheel as per FIG. 6 is designed for a maximum torque of approximately 75 mNm and has an idle torque of approximately 11 mNm.

Figure 7:
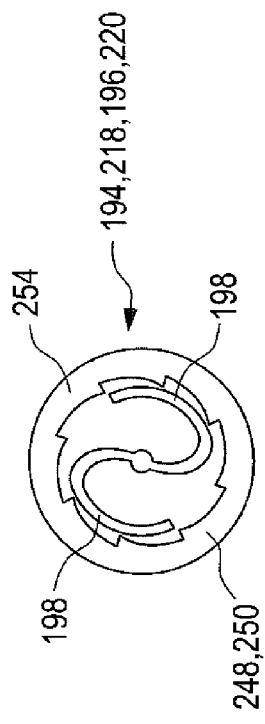

FIG. 7 shows an exemplary embodiment of a freewheel 196, 220 which is an alternative to that of FIG. 6. The freewheel 196, 220 once again has two freewheel arms 198 which in this exemplary embodiment likewise glide over a toothed structure 254 of the drive element 248, 250 to be driven. In this exemplary embodiment, the driving direction is a counterclockwise rotational direction of the freewheel arms 198. In contrast to FIG. 6, in the example in FIG. 7, provision is additionally made of a larger number of teeth 256 and this results in less dead travel. The freewheel 196, 220 according to FIG. 7 is designed for a maximum torque of approximately 20 mNm.

Figure 8B:
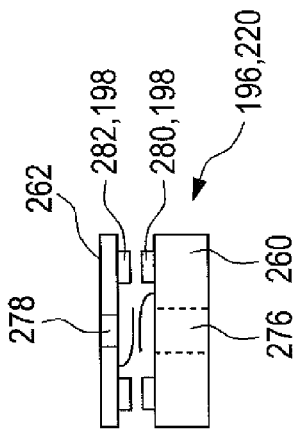
Figure 8A:
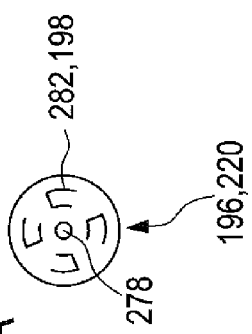

FIGS. 8A and 8B illustrate a further variant of a freewheel 196, 220 which can be produced entirely from sheet steel. Here, again, provision is made of a drive side 260 and an output side 262, which in this example are respectively made of circular sheet steel disks. FIG. 8A shows a plan view from above onto the output side 262, whereas FIG. 8B shows a side view of the freewheel 196, 220.

The disks respectively have a bore 276 or 278. Oppositely oriented freewheel arms 198 in the form of driver levers 280, 282 are stamped out of the disks, which driver levers have the shape of tongues. In this example, provision is made of respectively four such driver levers 280, 282, but this does not preclude an embodiment with a different number of levers. If the drive side 260 rotates counterclockwise in FIG. 8A, these tongue-shaped driver levers 280, 282 glide over one another and so there is no driving (idle). By contrast, in a clockwise rotation, the driver levers 280, 282 get caught in one another and there is driving.

This variant illustrated in FIGS. 8A and 8B permits a particularly flat design and, with two driver levers 198, is designed for a maximum torque of 50 mNm and an idle torque of approximately 2.8 mNm. In the illustrated variant with four freewheel arms 198, the freewheel 196, 220 is designed for a maximum torque of approximately 100 mNm and an idle torque of approximately 5.6 mNm.

Figure 9:
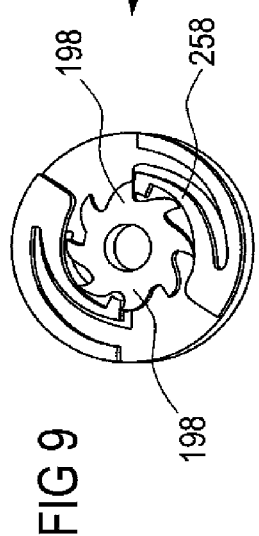

FIG. 9 illustrates a further exemplary embodiment of a freewheel 196, 220. Compared to the freewheel arms in the preceding exemplary embodiments, the freewheel arms 198 in this case are very much shorter and constitute a gearwheel structure with 8 teeth. Two driver arms 258 engage into these freewheel arms 198. The effect of these driver arms is that there is driving of the driver arms 258 if the freewheel 196, 220 rotates clockwise, but this is not the case during counter-clockwise rotation. The freewheel 196, 220 as per FIG. 9 is designed with 2 driver arms 258, i.e., as illustrated in FIG. 9, for a maximum torque of 25 mNm and an idle torque of approximately 4.4 mNm, and in a variant (not illustrated) with four driver arms 258 is designed for a maximum torque of approximately 40 mNm and an idle torque of approximately 6.6 mNm.

In the sampling system 110 described above on the basis of FIGS. 2A to 3D, at least one coupled system function therefore contains a transport function, namely the driving of the take-up reel 146. As can be seen, for example, in FIG. 2B, this drive is carried out via the reel gearwheel 224. In principle, a different form of reel drive is also feasible. In this case, the coupling of the reel drive to the take-up reel 146 can, for example, be effected rigidly, for example, by the take-up reel 146, for example, as a component of a tape cassette 158, being placed onto this reel drive in a rotationally secured fashion. Thus, for example, the reel drive can engage into one or more grooves in the inner region of the take-up reel 146 and so, when the reel drive, in particular the reel gearwheel 224, rotates, the take-up reel 146 is driven. However, in principle, a linear drive is also possible.

Figure 10:
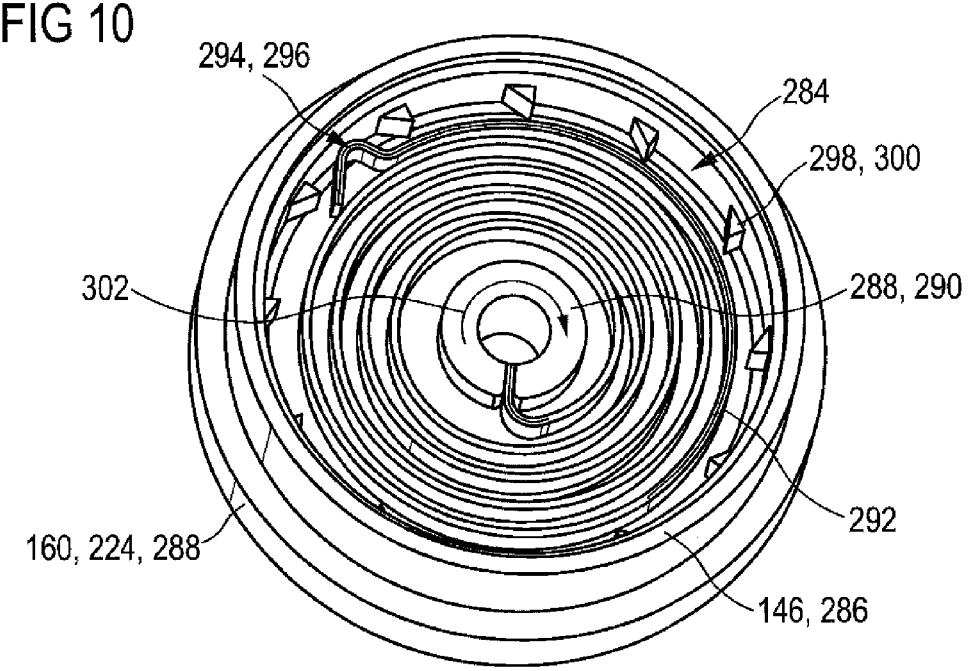
FIGS. 10 to 12 show different exemplary embodiments of slip couplings for driving a take-up reel.
Figure 11:
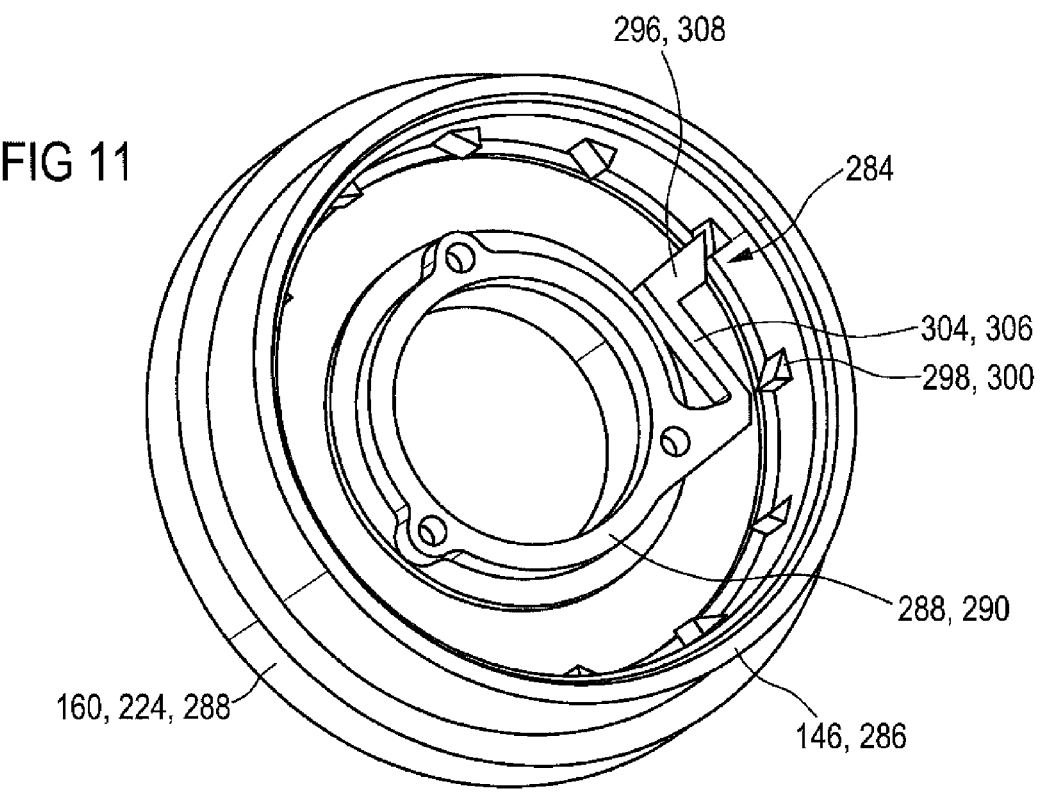
Figure 12:
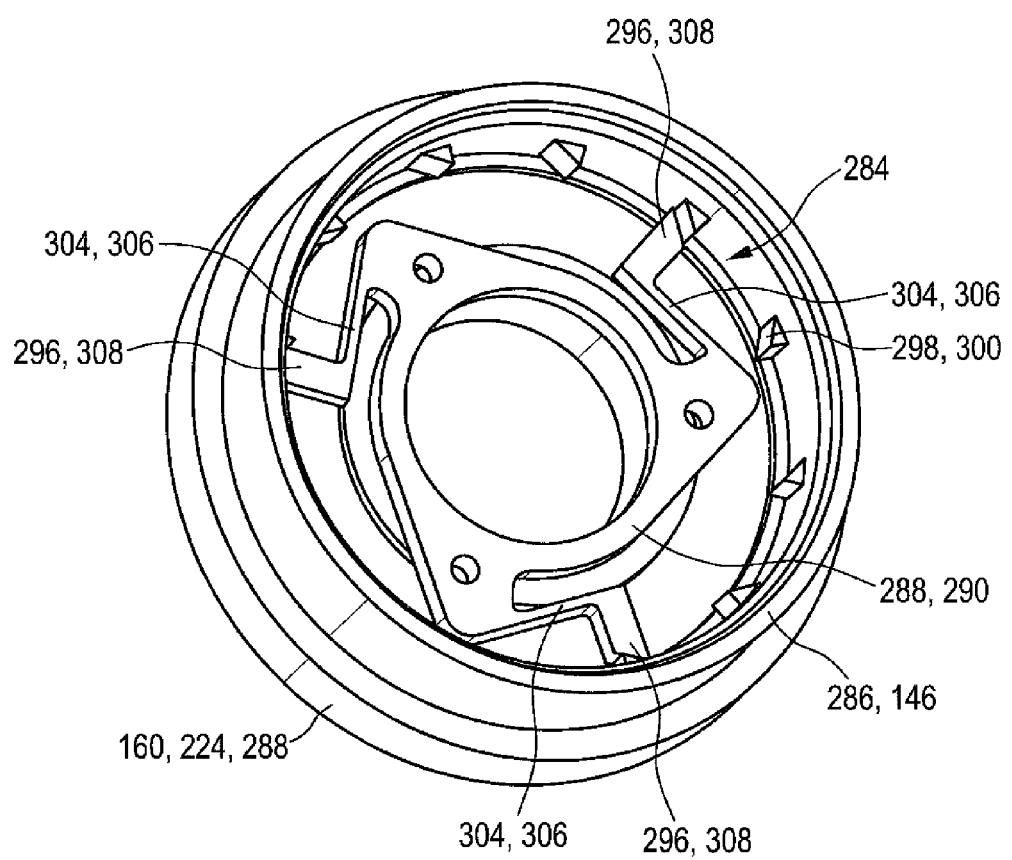

As an alternative to, or in addition to, a rotationally secured connection between reel drive and take-up reel 146, use can however also be made of one or more slip couplings, as illustrated above, which can be part of the drive unit 160, for example, part of the reel drive. Examples of such slip couplings are shown in FIGS. 10 to 12, which are intended to be explained in the following text. There, the slip couplings are generically referred to by reference sign 284.

In FIGS. 10 to 12, only one reel wheel 286 of the take-up reel 146 is illustrated in each case in order to permit a view of the slip coupling 284. The reel wheel 286 is driven by a reel drive 288 which is part of the drive unit 160 and can, for example, comprise the reel gearwheel 224. This reel drive 288 drives the reel wheel 286 onto which, in turn, the analysis tape 114 (not illustrated in the Figures) with the used test elements 122 and/or lancets 128 can be wound up. In the process, the reel wheel 286 can directly be a part of the take-up reel 146. However, alternatively, the take-up reel 146 can merely also be placed on this reel wheel 286.

In the illustrated exemplary embodiments, the slip coupling 284 is only partly a constituent of the drive unit 160 and comprises elements of the reel wheel 286 and of the reel drive 288. In the exemplary embodiment illustrated in FIG. 10, the slip coupling 284 comprises a spiral spring element 292 which is connected to a central hub 290 of the reel drive 288 and can, for example, be produced from a metallic material, for example, spring steel. However, in principle, other materials, e.g., plastic materials, can also be used. As explained below on the basis of further examples, the slip coupling 284 can however also comprise different types of spring elements.

The spiral spring element 292 ends in a bent end 294 which acts as a first engagement element 296. This first engagement element 296, which can also have a different design to that of a bent end 294, interacts with second engagement elements 298. In the exemplary embodiment illustrated in FIG. 10, these second engagement elements 298 are designed in the form of ramp-shaped teeth 300. However, in principle, a different design of these second engagement elements 298 is also possible.

If the reel drive 288 is rotated in one rotational direction 302, the first engagement element 296 first of all engages into the second engagement elements 298. In the process, the number of teeth 300 distributed over the inner circumference of the reel wheel 286 should in principle be selected to be as large as possible in order to achieve a dead travel which is as short as possible. In the illustrated exemplary embodiment, provision is made of eleven teeth 300, although, in principle, a different number of teeth 300 is also possible.

In the mentioned rotation in the rotational direction 302, the spiral spring element 292 drives the reel wheel 286 as a result of the engagement of the engagement elements 296, 298 until a desired positioning of the analysis tape 114 is achieved. By way of example, this positioning can consist of a certain test field 124 and/or a certain lancet 128, for example, the respectively next lancet 128 and/or the next test field 124, reaching the application position 118 and/or a measurement position. As described above, provision can be made in this application position 118 and/or measurement position of e.g., a blocking element which prevents onward transport of the analysis tape 114 and/or makes it more difficult. By way of example, this blocking element can in turn comprise at least a first engagement element which is fixedly connected to the sampling system, and a second engagement element which is connected to the analysis tape 114, with the two engagement elements engaging in one another and preventing onward transport when the desired application position and/or measurement position is reached. A gripper or another type of blocking element is also feasible. The blocking element then exerts a force onto the analysis tape 114; here this force corresponds to a holding force. This holding force is converted into a torque at the reel drive 288, which torque counteracts the driving torque of the reel drive 288. The spiral spring element 292 then contracts up to a defined maximum torque. This maximum torque is due to the fact that, during the interaction, the bent end 294 of the spiral spring element 292 wanders radially inward until the teeth 300 are no longer driven. From this torque, the first engagement element 296 disengages from the second engagement elements 298 and the slip coupling 284 opens. The bent end 294 of the spiral spring element 292 now slips over the teeth 300 on the reel wheel 286 and thus decouples the drive unit 160 from the take-up reel 146 and so the transport function is no longer performed. On the one hand, this prevents onward transport of the analysis tape 114 into an erroneous position and, on the other hand, damage to the analysis tape 114, the blocking element (e.g., a gripper) and/or the drive unit 160 can also be prevented. Furthermore, the changed drive conditions at different degrees of winding of the take-up reel 146 described above can be compensated for in this fashion.

As illustrated above, the slip coupling 284 shown in FIG. 10 is merely one of a number of possible exemplary embodiments. Thus, for example, the spiral spring element 292 can comprise a metallic spiral spring element and/or a plastics spiral spring element, which can, for example, be attached to the central hub 290 and/or to another element of the reel drive 288 in, for example, an interlocking, force-fit or cohesively bonding fashion. However, alternatively, the spring element can also be held on the element to be driven and so there can be a reversal of the principle shown in FIG. 10. Thus, for example, the reel drive 288 can comprise the second engagement elements 298, for example, in the form of teeth 300, and the reel wheel 286 to be driven can comprise the spring element, for example, the spiral spring element 292, with the first engagement element 296. A plurality of engagement elements 296 is also feasible.

FIGS. 11 and 12 illustrate alternative exemplary embodiments of slip couplings 284. In these alternative exemplary embodiments, the spiral spring element 292 as per the exemplary embodiment in FIG. 10 is replaced by spring elements 304 which in this case comprise a spring arm 306. Here, the exemplary embodiments as per FIGS. 11 and 12 differ in the number of these spring elements 304 or spring arms 306. Whereas the exemplary embodiment as per FIG. 11 only provides one spring arm 306, a plurality of spring arms 306 are present in the exemplary embodiment as per FIG. 12. By way of example, the spring arms 306, like remaining parts of the slip couplings 184 as well, can be produced from a metallic material and/or a plastics material. However, in principle, other materials, particularly materials with elastic properties, can also be used. In this exemplary embodiment as per FIG. 12, three spring arms 306 are distributed evenly along the circumference of the central hub 290 and connected to the latter. However, in principle, a different number and/or arrangement of the spring arms 306 is also possible.

In the exemplary embodiments shown in FIGS. 11 and 12, first engagement elements 296 are again provided at the end of the spring arms 306. In the illustrated exemplary embodiment, these first engagement elements 296 comprise projections 308 protruding radially from the spring arms 306. However, in principle, a different embodiment of the first engagement elements 296 is also possible.

The first engagement elements 296 in the form of projections 308 in turn interact with second engagement elements 298 in the form of teeth 300 which are arranged on the inner circumference of the reel wheel 286. By way of example, these teeth 300 can again be of a ramp-like design, wherein the outer surface of the projections 308 can, for example, be beveled and thus be designed substantially parallel to the ramp surfaces of the teeth 300. However, in principle, a non-parallel arrangement is also possible.

Here, the effect of the slip couplings 284 as per FIGS. 11 and 12 is, in principle, similar to the effect described on the basis of FIG. 10. Once again, the teeth 300 of the reel wheel 286 are driven by the projections 308 up to a maximum torque. However, if the counteracting torque with which the reel wheel 286 opposes this drive exceeds a maximum torque, the spring arms 306 are bent inward and the projections 308 move radially inward. The transport function is suspended above a maximum torque when the projections 308 no longer engage in the teeth 300 or the reel wheel 286 is no longer driven. Once again, this maximum torque can, for example, be provided by one or more blocking elements, for example, a gripper which holds the analysis tape 114 in a desired position.

As illustrated above, the slip couplings 284 shown in FIGS. 10 to 12 merely constitute possible embodiments of such slip couplings. Furthermore, reference is made to the fact that the option of using a slip coupling 284 for coupling onto the reel wheel 286 and the transport function of the latter merely constitutes one of several options for the expedient use of such slip couplings 284 in the sampling systems 110. By way of example, alternatively or additionally, the coupling of one or more other system functions can, for example, also be performed by one or more slip couplings 284. Furthermore, the drive unit 160 can, alternatively or additionally, also comprise one or more slip couplings 284 for other purposes, for example, in the drive of the coupling element 152 and/or in the coupling onto the energy transducer 162. Thus, for example, a slip coupling 284 can also be used expediently in the coupling onto the energy transducer 162, for example, to avoid damage to the drive unit 160 and/or further elements in the case of a malfunction of the energy transducer 162. Furthermore, a slip coupling 284 can, for example, also be used in the coupling onto the mechanical energy store 204, for example, to avoid over-tensioning of a piercing spring 206 and damage thereto as a result of this. Various additional refinements are feasible.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

| List of reference numerals | | | |
| --- | --- | --- | --- |
| 110 | Sampling system | 176 | First drive wheel |
| 112 | Analytic auxiliary means | 178 | Motor axle |
| 114 | Analysis tape | 180 | First drivetrain |
| 116 | Base plate | 182 | Second drivetrain |
| 118 | Application position | 184 | Piercing drive gearwheel |
| 120 | Supply reel | 186 | Release gearwheel |
| 122 | Test elements | 188 | Toothed circumferential region |
| 124 | Test fields | | |
| 126 | Carrier band | 190 | Untoothed circumferential region |
| 128 | Lancets | | |
| 130 | Pair of analytic auxiliary means | 192 | Axle |
| | | 194 | First rotational-direction sensitive element |
| 132 | Running direction of the analysis tape | | |
| | | 196 | First freewheel |
| 134 | Markings | 198 | Freewheel arms |
| 136 | Roller system | 200 | Lock |
| 138 | Fixed rollers | 201 | Catch |
| 140 | Moveable rollers | 202 | Piercing spring gearwheel |
| 142 | Deflection system | 203 | Catch ring |
| 144 | Unwinding direction | 204 | Mechanical energy store |
| 146 | Take-up reel | 205 | Bore |
| 148 | Winding direction | 206 | Piercing spring |
| 150 | Coupling piece | 208 | Axle |
| 152 | Coupling element | 210 | Eccentric bolt |
| 154 | Deflection direction | 212 | Reel drive gearwheel |
| 156 | Slit | 214 | Axle |
| 158 | Tape cassette | 216 | Transport gearwheel |
| 160 | Drive unit | 218 | Second rotational-direction |

-continued

List of reference numerals

| | | | |
|---|---|---|---|
| 162 | Motor | | sensitive element |
| 164 | Toothed transmission | 220 | Second freewheel |
| 166 | Connecting rod | 222 | Freewheel lock |
| 168 | Base plate | 224 | Reel gearwheel |
| 170 | Motor guide | 226 | Clockwise rotation of the motor gearwheel |
| 172 | Supports | | |
| 174 | Motor gearwheel | 280 | Driver lever |
| 228 | Rotation of the piercing drive gearwheel | 282 | Driver lever |
| | | 284 | Slip coupling |
| 230 | Piercing movement | 286 | Reel wheel |
| 232 | Counterclockwise rotation of the motor gearwheel | 288 | Reel drive |
| | | 290 | Central hub |
| 234 | Clockwise rotation of the reel drive gearwheel and transport gearwheel | 292 | Spiral spring element |
| | | 294 | Bent end |
| | | 296 | First engagement element |
| 236 | Counterclockwise rotation of the take-up reel | 298 | Second engagement elements |
| | | 300 | Teeth |
| 238 | Clockwise rotation of the piercing spring gearwheel | 302 | Rotational direction |
| | | 304 | Spring elements |
| 240 | Sampling movement | 306 | Spring arm |
| 242 | Rotational-direction sensitive element | 308 | Projections |
| 243 | Bolt | | |
| 244 | First drive plane | | |
| 246 | Second drive plane | | |
| 248 | Drive element of the first drivetrain | | |
| 250 | Drive element of the second drivetrain | | |
| 252 | Groove | | |
| 254 | Toothed structure | | |
| 256 | Teeth | | |
| 258 | Driver arms | | |
| 260 | Drive side | | |
| 262 | Output side | | |
| 264 | Finger | | |
| 266 | Axle | | |
| 268 | Flat flanks | | |
| 270 | Driver ends | | |
| 272 | Steep flanks | | |
| 274 | Second toothed structure | | |
| 275 | Channel | | |
| 276 | Bore | | |
| 278 | Bore | | |

What is claimed is:

1. A sampling system for collecting a liquid sample, comprising:
an analytic auxiliary means;
a coupling element for coupling to the analytic auxiliary means; and
a drive unit for driving a movement of the coupling element from a rest position into a deflected position, the drive unit comprising:
an energy transducer which rotates a first drive wheel in first and second rotational directions; and
a coupling device comprising a rotational-direction sensitive element for coupling to the first drive wheel and for transferring mechanical energy from the energy transducer to different subsystems;
wherein, the coupling device couples the first drive wheel to a first subsystem in the first rotational direction and couples the first drive wheel to a second subsystem in the second rotational direction; and
wherein the coupling device comprises a first drive element coupled to the first subsystem and/or the second subsystem, the first drive wheel and the first drive element being interconnected by the rotational-direction sensitive element, the rotational-direction sensitive element coupling the first drive wheel to the first drive element in the first rotational direction and decoupling the first drive wheel from the first drive element in the second rotational direction.

2. The sampling system of claim 1, wherein the first subsystem comprises a subsystem of the sampling system selected from the following group:
a drive for a piercing movement of a lancet of the analytic auxiliary means;
a means for driving a sampling movement of a test element of the analytic auxiliary means;
a means for tensioning a spring element for driving the piercing movement of the lancet;
a means for transporting an analytic auxiliary means for providing the analytic auxiliary means in an application position;
a means for transporting an analytic auxiliary means for providing the analytic auxiliary means in a measurement position;
a means for transporting a cartridge of the sampling system for providing an analytic auxiliary means from a cartridge in an application position;
a means for transporting an analysis tape comprising a number of analytic auxiliary means for providing an analytic auxiliary means in an application position; and
a means for transporting an analysis disk comprising a number of analytic auxiliary means for providing an analytic auxiliary means in an application position.

3. The sampling system of claim 2, wherein the second subsystem comprises a subsystem of the sampling system selected from the following group:
a drive for a piercing movement of a lancet of the analytic auxiliary means;
a means for driving a sampling movement of a test element of the analytic auxiliary means;
a means for tensioning a spring element for driving the piercing movement of the lancet;
a means for transporting an analytic auxiliary means for providing the analytic auxiliary means in an application position;
a means for transporting an analytic auxiliary means for providing the analytic auxiliary means in a measurement position;
a means for transporting a cartridge of the sampling system for providing an analytic auxiliary means from a cartridge in an application position;
a means for transporting an analysis tape comprising a number of analytic auxiliary means for providing an analytic auxiliary means in an application position; and
a means for transporting an analysis disk comprising a number of analytic auxiliary means for providing an analytic auxiliary means in an application position.

4. The sampling system of claim 1, wherein the analytic auxiliary means comprises at least one of a lancet and a test element with a test field for analyzing the liquid sample.

5. The sampling system of claim 4, wherein the analytic auxiliary means comprises an analysis tape having a multiplicity of alternately arranged lancets and test fields.

6. The sampling system of claim 1, wherein the coupling element comprises a drive configured to couple to an analytic auxiliary means arranged in an application position, the drive comprising one of a connecting rod drive and a crank drive.

7. The sampling system of claim 1, wherein the energy transducer comprises an electric motor.

8. The sampling system of claim 1, further comprising a mechanical energy store configured to emit energy for a piercing movement of a lancet of the analytic auxiliary means.

9. The sampling system of claim 8, wherein the mechanical energy store comprises one of a helical spring, a spiral spring, a leaf spring, a cup spring, an elastic element, an elastomeric element and a pneumatic pressure store.

10. The sampling system of claim 8, wherein the drive unit has a toothed transmission configured to charge the mechanical energy store in a first angular position range of the energy transducer and to maintain said store in a charged state, the toothed transmission further configured to release the mechanical energy store in a second angular position range to thereby emit energy for the piercing movement of the lancet.

11. The sampling system of claim 10, wherein the toothed transmission has at least one partly toothed gearwheel which is toothed in at least a first circumferential region and which is not toothed in at least a second circumferential region.

12. The sampling system of claim 11, wherein the toothed transmission comprises a lock configured to prevent discharge of the energy store in the first angular position range.

13. The sampling system of claim 11, further comprising a lock for keeping the mechanical energy store in the charged state.

14. The sampling system of claim 1, comprising an element configured to hold a plurality of analytic test elements, the element selected from the following group: a drum cartridge, a rod cartridge, a row cartridge, a tape cassette, a staggered cartridge, an analysis tape and an analysis disk.

15. The sampling system of claim 1, wherein the drive unit comprises a toothed gear system comprising a transmission element selected from the following group: a spur gear transmission; a bevel gear transmission; a worm gear transmission; a rack-and-pinion gear transmission; a spindle gear transmission; a contrate gear transmission; and a planetary gear transmission.

16. The sampling system of claim 1, wherein the coupling device comprises a second drive element connected to a second drive wheel by a second rotational-direction sensitive element, the first and second rotational-direction sensitive elements having opposing rotational-direction sensitivities and the first and second drive elements respectively being coupled to different subsystems.

17. The sampling system of claim 1, wherein the rotational-direction sensitive element comprises a freewheel selected from the following group: a clamping roller freewheel, a clamping body freewheel, a catch freewheel, a frictional-locking mechanism freewheel and a finger freewheel.

18. The sampling system of claim 17, wherein the freewheel has a freewheel lock for reducing a freewheel dead travel.

19. The sampling system of claim 1, wherein the first drive wheel is arranged on a first plane in the first rotational direction and coupled to the first drive element, the first drive wheel being arranged on a second plane in the second rotational direction and coupled to a second drive element.

20. The sampling system of claim 1, wherein the energy transducer is, in the first or second rotational directions, simultaneously coupled to a subsystem in which a mechanical energy store is charged with energy and to a subsystem in which a test element is transferred into a deflected position.

21. The sampling system of claim 20, wherein the energy transducer is, in the second rotational direction, coupled to a subsystem in which an analytic auxiliary means is provided in an application position.

22. The sampling system of claim 1, wherein during operation the sampling system performs a sequence of first, second, third and fourth rotational movements of the energy transducer wherein:
   a) the first rotational movement of the energy transducer is in the first rotational direction and releases a mechanical energy store and thereby emits energy for a piercing movement of a lancet of the analytic auxiliary means;
   b) the second rotational movement of the energy transducer is in the second rotational direction and transfers a test element with a test field for analyzing the liquid sample into the application position;
   c) the third rotational movement of the energy transducer is in the first rotational direction and charges the mechanical energy store with energy and transfers the test element into a deflected position; and
   d) the fourth rotational movement of the energy transducer is in the second rotational direction and transfers a lancet into the application position.

23. The sampling system of claim 22, wherein during operation of the sampling system, the sampling system further performs a transport step in which the test element is transferred into a measurement position.

24. The sampling system of claim 23, wherein the sampling system performs the transport step between the second and third rotational movements.

25. The sampling system of claim 1, wherein the drive unit comprises a slip coupling.

26. The sampling system of claim 1, further comprising a tape cassette having an analysis tape, a supply reel and a take-up reel for holding the analysis tape and a coupling piece.

* * * * *